(12) United States Patent
Quincy, III et al.

(10) Patent No.: US 12,343,243 B2
(45) Date of Patent: Jul. 1, 2025

(54) ABSORBENT ARTICLE WITH THREE DIMENSIONAL SHAPE RETAINING STRUCTURE

(71) Applicant: Kimberly-Clark Worldwide, Inc., Neenah, WI (US)

(72) Inventors: Roger B. Quincy, III, Cumming, GA (US); Andrew T. Hammond, Grand Chute, WI (US); Prasad S. Potnis, Johns Creek, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1558 days.

(21) Appl. No.: 15/557,256

(22) PCT Filed: Mar. 30, 2015

(86) PCT No.: PCT/US2015/023298
§ 371 (c)(1),
(2) Date: Sep. 11, 2017

(87) PCT Pub. No.: WO2016/159952
PCT Pub. Date: Oct. 6, 2016

(65) Prior Publication Data
US 2018/0049928 A1    Feb. 22, 2018

(51) Int. Cl.
*A61F 13/511* (2006.01)
*A61F 13/537* (2006.01)
*A61F 13/539* (2006.01)

(52) U.S. Cl.
CPC ............ *A61F 13/51104* (2013.01); *A61F 13/53704* (2013.01); *A61F 13/53747* (2013.01);
(Continued)

(58) Field of Classification Search
CPC .......... A61F 13/51104; A61F 13/53704; A61F 13/53747; A61F 13/539; A61F 2013/53782; A61F 2013/53908
See application file for complete search history.

(56) References Cited

U.S. PATENT DOCUMENTS 2,877,765 A    3/1959    Bunyan
3,307,545 A    3/1967    Surowitz
(Continued)

FOREIGN PATENT DOCUMENTS

CN    1346253 A     4/2002
CN    101282757 A   10/2008
(Continued)

OTHER PUBLICATIONS

Definition of emboss, Merriam-Webster Dictionary, merriam-webster.com/dictionary/emboss (Year: 2020).*
(Continued)

*Primary Examiner* — Jessica Arble
(74) *Attorney, Agent, or Firm* — KIMBERLY-CLARK WORLDWIDE, INC.

(57) ABSTRACT

An absorbent article (10) can include a body facing liner (28), a backsheet (26), and an absorbent body (34) disposed between the body facing liner (28) and the backsheet (26). The body facing liner (28) can include at least one embossment (64). The absorbent article (10) can also include an acquisition layer (70, 170, 270, 370, 470) including a body facing surface (70a) and a garment facing surface (70b). The acquisition layer (70, 170, 270, 370, 470) can include at least one recess (90). The at least one recess (90) can receive the at least one embossment (64) in a nested configuration. In some embodiments, the embossment (64) can include an intersecting slit formation (78).

2 Claims, 11 Drawing Sheets

(52) U.S. Cl.
CPC .................. *A61F 13/539* (2013.01); *A61F 2013/53782* (2013.01); *A61F 2013/53908* (2013.01)

(56) References Cited

U.S. PATENT DOCUMENTS

| | | | |
|---|---|---|---|
| 3,814,101 A | 6/1974 | Kozak | |
| 3,886,941 A | 6/1975 | Duane et al. | |
| 3,929,135 A | 12/1975 | Thompson | |
| 4,041,951 A | 8/1977 | Sanford | |
| 4,252,516 A | 2/1981 | Raley et al. | |
| 4,276,338 A | 6/1981 | Ludwa et al. | |
| 4,395,215 A | 7/1983 | Bishop | |
| 4,591,523 A | 5/1986 | Thompson | |
| 4,609,518 A | 9/1986 | Curro et al. | |
| 4,614,679 A | 9/1986 | Farrington, Jr. et al. | |
| 4,626,254 A | 12/1986 | Widlund et al. | |
| 4,634,440 A | 1/1987 | Widlund et al. | |
| 4,637,819 A | 1/1987 | Ouellette et al. | |
| 4,704,112 A | 11/1987 | Suzuki et al. | |
| 4,761,322 A | 8/1988 | Raley | |
| 4,780,352 A | 10/1988 | Palumbo | |
| 4,886,632 A | 12/1989 | Van Iten et al. | |
| 5,078,710 A | 1/1992 | Suda et al. | |
| 5,180,620 A | 1/1993 | Mende | |
| 5,268,213 A | 12/1993 | Murakami et al. | |
| 5,387,209 A | 2/1995 | Yamamoto et al. | |
| 5,397,316 A | 3/1995 | Young et al. | |
| 5,449,352 A | 9/1995 | Nishino et al. | |
| 5,500,270 A | 3/1996 | Langdon et al. | |
| 5,514,105 A | 5/1996 | Goodman, Jr. et al. | |
| 5,536,555 A | 7/1996 | Zelazoski et al. | |
| 5,648,142 A | 7/1997 | Phillips | |
| 5,885,267 A | 3/1999 | Mishima et al. | |
| 5,895,380 A | 4/1999 | Turi et al. | |
| 5,935,682 A | 8/1999 | Wallstroem | |
| 6,274,218 B1 | 8/2001 | Shimizu | |
| 6,410,823 B1 | 6/2002 | Daley et al. | |
| 6,479,130 B1 | 11/2002 | Takai et al. | |
| 6,479,415 B1* | 11/2002 | Erspamer ............... A61F 13/534 442/381 | |
| 6,534,149 B1 | 3/2003 | Daley et al. | |
| 6,739,024 B1 | 5/2004 | Wagner | |
| 6,837,956 B2 | 1/2005 | Cowell et al. | |
| 7,323,072 B2 | 1/2008 | Engelhart et al. | |
| 7,371,919 B1 | 5/2008 | Busam et al. | |
| 8,088,316 B2 | 1/2012 | Muth et al. | |
| 8,708,687 B2 | 4/2014 | Coe et al. | |
| 2001/0037103 A1 | 11/2001 | Onishi | |
| 2002/0026168 A1 | 2/2002 | Yagou et al. | |
| 2002/0182396 A1 | 12/2002 | Delucia et al. | |
| 2003/0045851 A1 | 3/2003 | Vartiainen | |
| 2003/0056893 A1 | 3/2003 | Delucia et al. | |
| 2003/0085213 A1 | 5/2003 | Burckhardt et al. | |
| 2003/0201582 A1 | 10/2003 | Gray | |
| 2004/0209041 A1 | 10/2004 | Muth et al. | |
| 2007/0073254 A1 | 3/2007 | Ponomarenko et al. | |
| 2007/0073256 A1* | 3/2007 | Ponomarenko ....... A61F 13/495 604/385.13 | |
| 2007/0135787 A1* | 6/2007 | Raidel ............... A61F 13/15723 604/383 | |
| 2008/0138574 A1 | 6/2008 | Maschino et al. | |
| 2009/0062760 A1 | 3/2009 | Wright et al. | |
| 2009/0302504 A1 | 12/2009 | Di Berardino | |
| 2010/0228215 A1 | 9/2010 | Ponomarenko et al. | |
| 2010/0312212 A1 | 12/2010 | Bond et al. | |
| 2012/0136329 A1* | 5/2012 | Carney ............ A61F 13/53704 604/383 | |
| 2012/0273997 A1 | 11/2012 | Stone et al. | |
| 2015/0065981 A1* | 3/2015 | Roe ................... A61F 13/53717 604/378 | |

FOREIGN PATENT DOCUMENTS

| | | |
|---|---|---|
| EP | 0 532 937 A1 | 3/1993 |
| FR | 2 397 797 A1 | 2/1979 |
| GB | 2 014 508 A1 | 8/1979 |
| JP | 02-019153 A | 1/1990 |
| JP | 02-198551 A | 8/1990 |
| WO | WO 1991/010415 A2 | 7/1991 |
| WO | WO 2009/062998 A1 | 5/2009 |
| WO | WO 2014/147498 A1 | 9/2014 |

OTHER PUBLICATIONS

Definition of punch, Merriam-Webster Dictionary, merriam-webster.com/dictionary/punch (Year: 2020).*

* cited by examiner

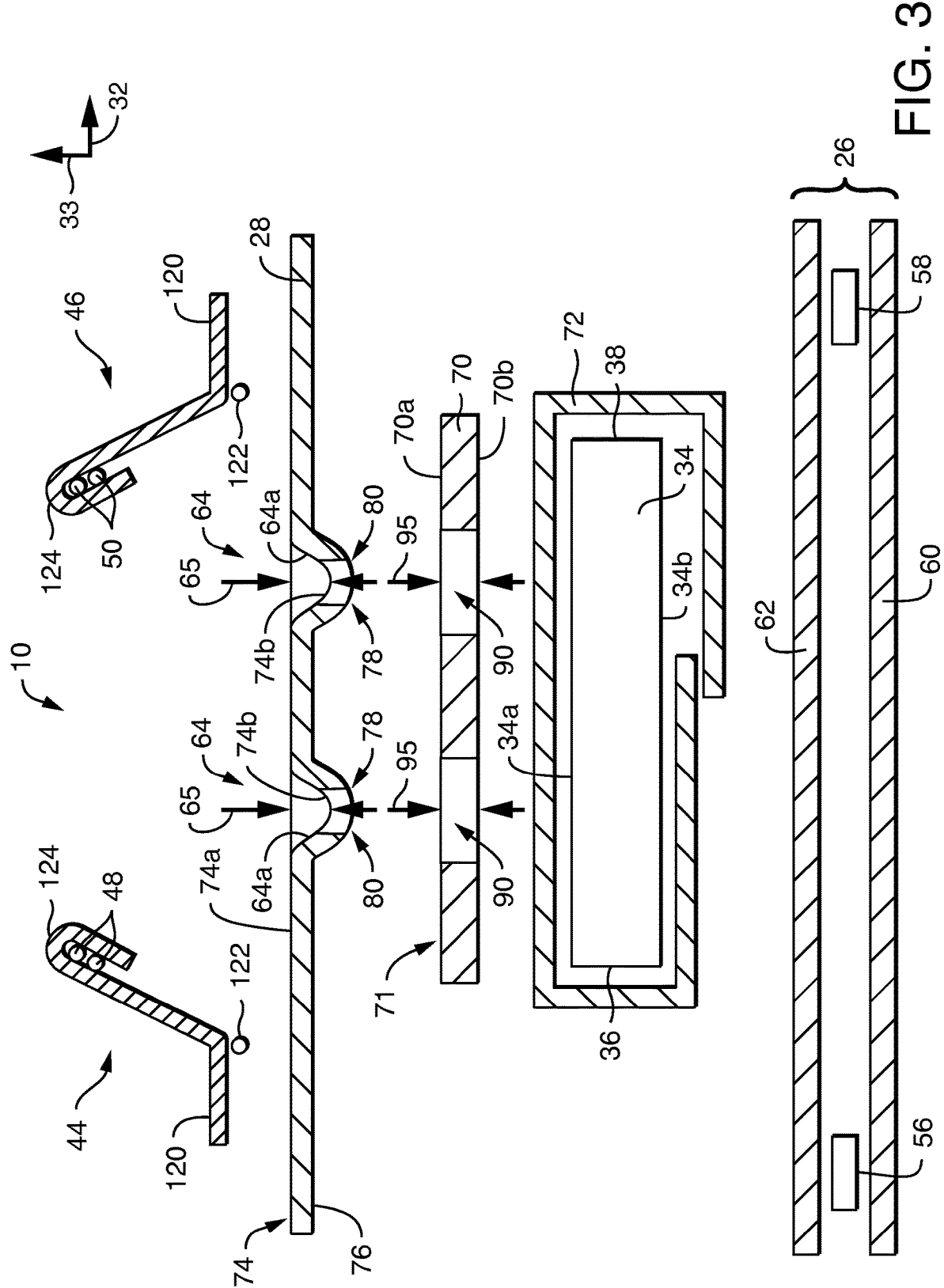

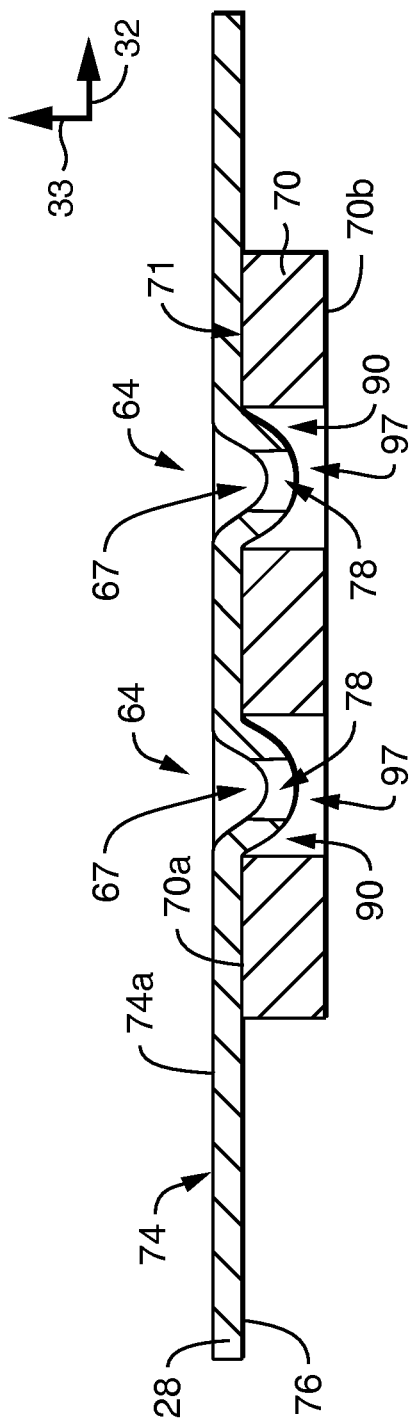
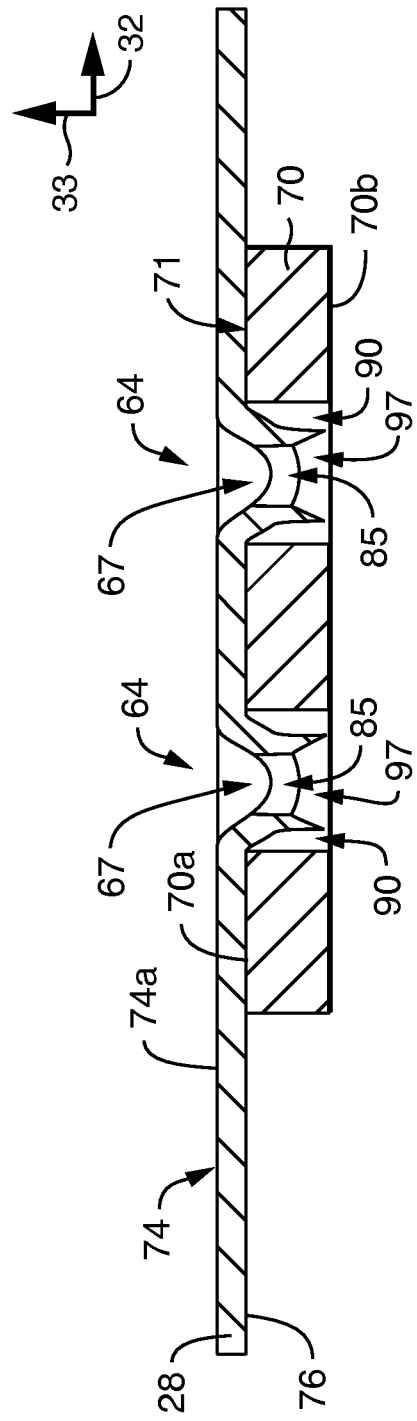

ABSORBENT ARTICLE WITH THREE DIMENSIONAL SHAPE RETAINING STRUCTURE

TECHNICAL FIELD

The present disclosure relates to absorbent articles.

BACKGROUND OF THE DISCLOSURE

One of the primary functions of personal care absorbent articles is to retain and absorb body exudates such as urine, fecal material, blood, and menses. Along these lines, a desired attribute of personal care absorbent articles is to minimize the leakage of such exudates from the absorbent article. It is also desired, however, that personal care absorbent articles retain and absorb the body exudates in such a fashion so as to provide a dry feel to the wearer, removing exudates from against the skin at the time of the initial insult of the exudate as well as retaining them away from the skin after such insult.

Absorbent articles, however, traditionally fail to possess the combination of the desired attributes. Absorbent articles commonly fail before the total absorbent capacity of the absorbent article is utilized. Problems which can typically exist can relate to the ability of the body facing liner to allow quick intake in one direction towards an absorbent body while preventing return of fluid in the opposite direction. Additionally, the rate at which intake occurs sometimes determines whether leakage is reduced or whether body fluids are appropriately contained.

Especially troublesome can be semi-solid fecal material, such as low viscosity fecal material which can be prevalent with younger children, and menses. Such body exudates have difficulty penetrating the body facing material of the absorbent article as easily as low viscosity exudates, such as urine, and tend to spread across the surface of the body facing material. These exudates can move around on the body facing material of an absorbent article under the influence of gravity, motion, and pressure by the wearer of the absorbent article. The migration of the exudates is often towards the perimeter of the absorbent article, increasing the likelihood of leakage and smears against the skin of the wearer which can make clean-up of the skin difficult.

There remains a need for an absorbent article that can adequately reduce the incidence of leakage of body exudates from the absorbent article. There remains a need for an absorbent article which can provide improved handling of body exudates. There remains a need for an absorbent article that can minimize the amount of body exudates in contact with the wearer's skin. There remains a need for an absorbent article that can provide physical and emotional comfort to the wearer of the absorbent article.

SUMMARY OF THE DISCLOSURE

In one embodiment, an absorbent article can include a longitudinal axis and a lateral axis. The absorbent article can include a front waist region, a rear waist region, and a crotch region. The crotch region can be disposed between the front waist region and the rear waist region. The absorbent article can further include a front waist edge in the front waist region, a rear waist edge in the rear waist region, and a first longitudinal side edge and a second longitudinal side edge. The first longitudinal side edge and the second longitudinal side edge can each extend from the front waist edge to the rear waist edge. The absorbent article can also include a body facing liner including a body facing surface and a garment facing surface. The body facing liner can include at least one embossment. The absorbent article can additionally include a backsheet and an absorbent body disposed between the body facing liner and the backsheet. Furthermore, the absorbent article can include an acquisition layer including a body facing surface and a garment facing surface. The body facing surface of the acquisition layer can include a planar portion. The acquisition layer can include at least one recess that does not extend from the body facing surface of the acquisition layer to the garment facing surface of the acquisition layer. The at least one recess can receive the at least one embossment of the body facing liner in a nested configuration.

In another embodiment, an absorbent article can include a longitudinal axis and a lateral axis. The absorbent article can include a front waist region, a rear waist region, and a crotch region. The crotch region can be disposed between the front waist region and the rear waist region. The absorbent article can further include a front waist edge in the front waist region, a rear waist edge in the rear waist region, and a first longitudinal side edge and a second longitudinal side edge. The first longitudinal side edge and the second longitudinal side edge can each extend from the front waist edge to the rear waist edge. The absorbent article can also include a body facing liner including a body facing surface and a garment facing surface. The body facing liner can include at least one embossment. The embossment can include an intersecting slit formation. The absorbent article can additionally include a backsheet and an absorbent body disposed between the body facing liner and the backsheet. Furthermore, the absorbent article can include an acquisition layer including a body facing surface and a garment facing surface. The acquisition layer can include at least one recess. The at least one recess can receive the at least one embossment of the body facing liner in a nested configuration.

BRIEF DESCRIPTION OF DRAWINGS

A full and enabling disclosure thereof, directed to one of ordinary skill in the art, is set forth more particularly in the remainder of the specification, which makes reference to the appended figures in which:

FIG. 3 is a cross-section, exploded view of the absorbent article taken along line 3-3 in FIG. 2.

FIG. 4A is a cross-section view of the body facing liner and the acquisition layer of FIG. 2 taken along line 3-3 in FIG. 2.

FIG. 4B is a cross-section view of the body facing liner and the acquisition layer of FIG. 2 similar to FIG. 4A, but shown immediately after an insult, with the intersecting slit formations being displaced from the plane of the body facing liner.

Figure 1:
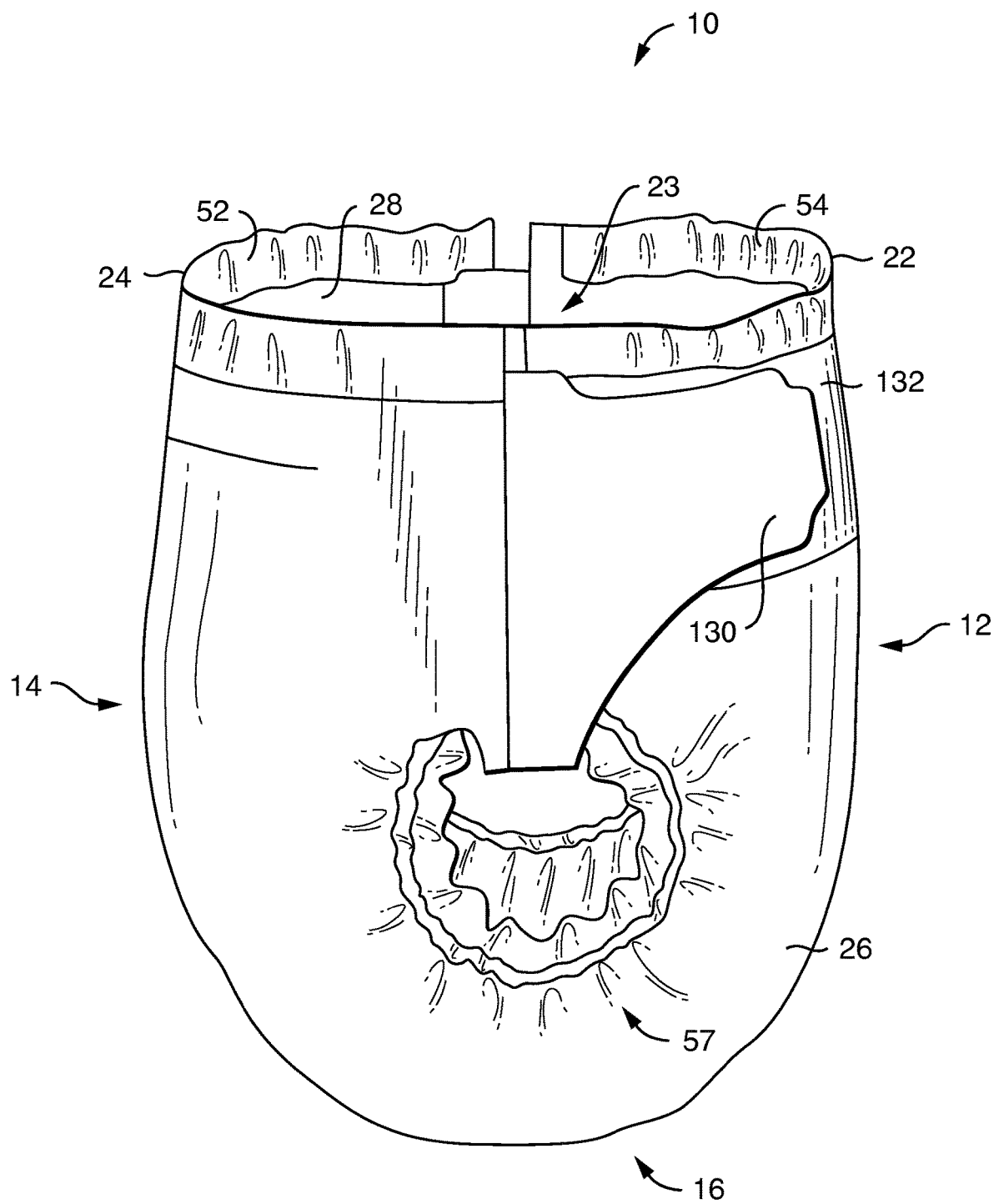
FIG. 1 is a side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article that can have a body facing liner with embossments and an acquisition layer with recesses. The recesses in the acquisition layer can help protect the embossments, and thus, the three-dimensional nature of the absorbent intake structure. Each example is provided by way of explanation and is not meant as a limitation. For example, features illustrated or described as part of one embodiment or figure can be used on another embodiment or figure to yield yet another embodiment. It is intended that the present disclosure include such modifications and variations.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting, distributing, and temporarily holding liquid body exudates to decelerate and diffuse an insult of liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" refers herein to one who fits an absorbent article, such as, but not limited to, a diaper, training pant, youth pant, incontinent product, or other absorbent article about the wearer of one of these absorbent articles. A user and a wearer can be one and the same person.

Figure 2:
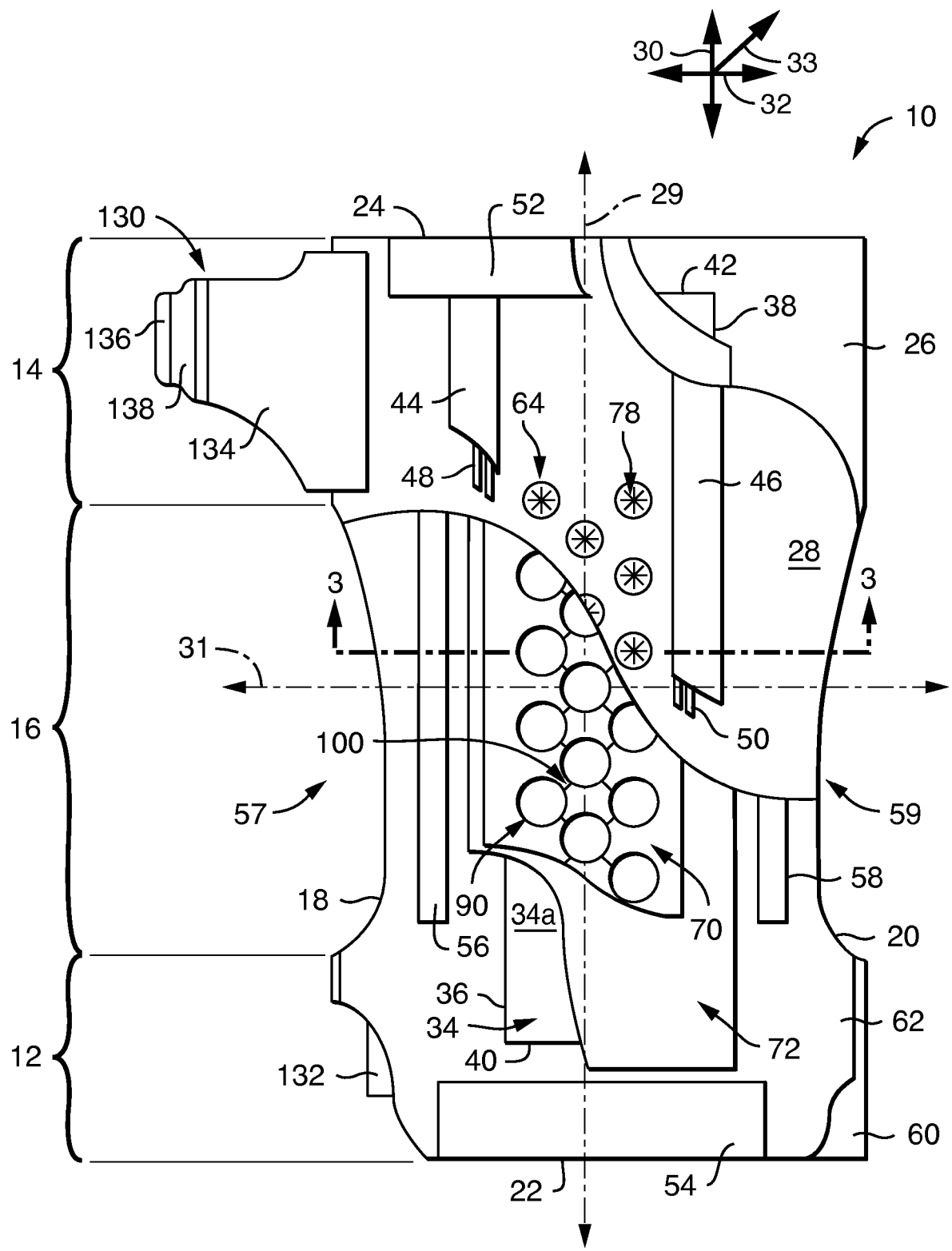
FIG. 2 is a top plan view of the absorbent article of FIG. 1 in an unfastened, stretched, and laid flat condition with the body facing surface of the absorbent article which contacts the wearer facing the viewer, portions of the absorbent article being cut away for clarity of illustration.

Absorbent Article:

Referring to FIGS. 1 and 2, a non-limiting illustration of an absorbent article 10, for example, a diaper, is illustrated. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIGS. 1 and 2 includes a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. The absorbent article 10 has a pair of longitudinal side edges, 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define the central waist opening 23. Portions of the longitudinal side edges, 18 and 20, in the crotch region 16 can generally define leg openings when the absorbent article 10 is worn.

The absorbent article 10 can include a backsheet 26 and a body facing liner 28. In an embodiment, the body facing liner 28 can be bonded to the backsheet 26 in a superposed relation by any suitable means such as, but not limited to, adhesives, ultrasonic bonds, thermal bonds, pressure bonds, or other conventional techniques. As will be discussed in further detail below, the body facing liner 28 can include at least one embossment 64 and at least one intersecting slit formation 78. The backsheet 26 can define a length in a longitudinal direction 30, and a width in the lateral direction 32, which, in the illustrated embodiment, can coincide with the length and width of the absorbent article 10. As illustrated in FIG. 2, the absorbent article 10 can have a longitudinal axis 29 extending in the longitudinal direction 30 and a lateral axis 31 extending in the lateral direction 32.

FIG. 2 illustrates the absorbent article 10 with certain portions cut-away for illustrating additional aspects of the absorbent article 10. An absorbent body 34 can be disposed between the backsheet 26 and the body facing liner 28. The absorbent body 34 can have longitudinal edges, 36 and 38, which, in an embodiment, can form portions of the longitudinal side edges, 18 and 20, respectively, of the absorbent article 10 and can have opposite end edges, 40 and 42, which, in an embodiment, can form portions of the waist edges, 22 and 24, respectively, of the absorbent article 10. In an embodiment, the absorbent body 34 can have a length and width that are the same as or less than the length and width of the absorbent article 10. The absorbent article 10 can also include an acquisition layer 70 and a fluid transfer layer 72. The acquisition layer 70 can include at least one recess 90.

The absorbent article 10 can be configured to contain and/or absorb liquid, solid, and semi-solid body exudates discharged from the wearer. For example, containment flaps, 44 and 46, can be configured to provide a barrier to the lateral flow of body exudates. As illustrated in FIG. 3, each containment flap 44, 46 can include elastic members 48, 50. The elastic members 48, 50 can include one or more elastic strands (two are shown in FIG. 3) that are aligned substantially parallel to the longitudinal axis 29 of the absorbent article 10. The containment flaps 44, 46 are laterally spaced from one another, such that the containment flap 44 is on one side of the longitudinal axis 29 and the containment flap 46 is on an opposite side of the longitudinal axis 29. The containment flaps 44, 46 can be attached to the absorbent article by being bonded to the body facing liner 28. The containment flaps, 44 and 46, can be located laterally inward from the longitudinal side edges, 18, 20 of the absorbent article 10, and can extend longitudinally along the entire length of absorbent article 10 or can extend partially along the length of the absorbent article 10.

To further enhance containment and/or absorption of body exudates, the absorbent article 10 can suitably include a rear waist elastic member 52, a front waist elastic member 54, and leg elastic members, 56 and 58, as are known to those skilled in the art. The waist elastic members, 52 and 54, can be attached to the backsheet 26 and/or the body facing liner 28 along or near the opposite waist edges, 24 and 22, and can extend over part or all of the waist edges, 24 and 22. In an embodiment shown in FIG. 2, the rear waist elastic member 52 is attached to the body facing liner 28 and the containment flaps 44, 46 and the front waist elastic member 54 is attached to the backsheet 26. The leg elastic members, 56 and 58, can be attached to the backsheet 26 and/or the body facing liner 28 along the opposite longitudinal side edges, 18 and 20, and positioned in the crotch region 16 of the absorbent article 10.

Additional details regarding each of these elements of the absorbent article 10 described herein can be found below and with reference to the FIGS. 1 through 12.

Backsheet:

The backsheet 26 and/or portions thereof can be breathable and/or liquid impermeable. The backsheet 26 and/or portions thereof can be elastic, stretchable, or non-stretchable. The backsheet 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the backsheet 26 can be constructed of a microporous polymeric film, such as polyethylene or polypropylene.

In an embodiment, the backsheet 26 can be a single layer of a liquid impermeable material. In an embodiment, the backsheet 26 can be suitably stretchable, and more suitably elastic, in at least the lateral or circumferential direction 32 of the absorbent article 10. In an embodiment, the backsheet 26 can be stretchable, and more suitably elastic, in both the lateral 32 and the longitudinal 30 directions. In an embodiment, the backsheet 26 can be a multi-layered laminate in which at least one of the layers is liquid impermeable. In an embodiment, the backsheet 26 can be a two layer construction, including an outer layer 60 material and an inner layer 62 material (such as shown in FIGS. 2 and 3) which can be bonded together such as by a laminate adhesive. Suitable laminate adhesives can be applied continuously or intermittently as beads, a spray, parallel swirls, or the like. Suitable adhesives can be obtained from Bostik Findlay Adhesives, Inc. of Wauwatosa, WI, U.S.A. It is to be understood that the inner layer 62 can be bonded to the outer layer 60 by other bonding methods, including, but not limited to, ultrasonic bonds, thermal bonds, pressure bonds, or the like.

The outer layer 60 of the backsheet 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 60 of a backsheet 26 can be a 20 gsm spunbond polypropylene non-woven web. The outer layer 60 may also be constructed of the same materials from which the body facing liner 28 can be constructed as described herein.

The liquid impermeable inner layer 62 of the backsheet 26 (or the liquid impermeable backsheet 26 where the backsheet 26 is of a single-layer construction) can be either vapor permeable (i.e., "breathable") or vapor impermeable. The liquid impermeable inner layer 62 (or the liquid impermeable backsheet 26 where the backsheet 26 is of a single-layer construction) may be manufactured from a thin plastic film, although other liquid impermeable materials may also be used. The liquid impermeable inner layer 62 (or the liquid impermeable backsheet 26 where the backsheet 26 is of a single-layer construction) can inhibit liquid body exudates from leaking out of the absorbent article 10 and wetting articles, such as bed sheets and clothing, as well as the wearer and caregiver. An example of a material for a liquid impermeable inner layer 62 (or the liquid impermeable backsheet 26 where the backsheet 26 is of a single-layer construction) can be a printed 19 gsm Berry Plastics XP-8695H film or equivalent commercially available from Berry Plastics Corporation, Evansville, IN, U.S.A.

Where the backsheet 26 is of a single layer construction, it can be embossed and/or matte finished to provide a more cloth-like texture or appearance. The backsheet 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer and the liquid loading imparted by the intended use of the absorbent article 10. Additionally, the size and the absorbent capacity of the absorbent body 34 can be varied to accommodate wearers ranging from infants to adults. For example, in some embodiments, the absorbent body 34 can have a length ranging from about 150 mm to about 520 mm, and the absorbent body 34 can have a crotch region 16 width ranging from about 30 mm to about 180 mm. In various embodiments, the width of the absorbent body 34 located within the front waist region 12 and/or the back waist region 14 of the absorbent article 10 can range from about 50 mm to about 130 mm. As noted herein, the absorbent body 34 can have a length and width that can be less than or equal to the length and width of the absorbent article 10.

In an embodiment, the absorbent article 10 can be an adult incontinence garment having the following ranges of lengths and widths of an absorbent body 34 having a rectangular shape: the length of the absorbent body 34 can range from about 400, 410 or 415 to about 425 or 450 mm; the width of the absorbent body 34 in the crotch region 16 can range from about 90, or 95 mm to about 100, 105, or 110 mm. It should be noted that the absorbent body 34 of an adult incontinence garment may or may not extend into either or both the front waist region 12 or the back waist region 14 of the absorbent article 10.

The absorbent body 34 can have two surfaces such as a body facing surface 34a and a garment facing surface 34b.

Edges, such as longitudinal side edges, 36 and 38, and such as front and back end edges, 40 and 42, can connect the two surfaces, 34a and 34b.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In some embodiments, the basis weight of the absorbent body 34 can be greater than about 200 gsm. In other embodiments, the basis weight of the absorbent body 34 can be greater than about 300 gsm.

In an embodiment, the absorbent body 34 may be constructed of a single layer of materials, or in the alternative, may be constructed of two or more layers of materials. In an embodiment in which the absorbent body 34 has two layers, the absorbent body 34 can have a wearer facing layer suitably composed of hydrophilic fibers and a garment facing layer suitably composed at least in part of a high absorbency material commonly known as superabsorbent material. In such an embodiment, the wearer facing layer of the absorbent body 34 can be suitably composed of cellulosic fluff, such as wood pulp fluff, and the garment facing layer of the absorbent body 34 can be suitably composed of superabsorbent material, or a mixture of cellulosic fluff and superabsorbent material. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that, in an embodiment, the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 34 with a lower absorbent capacity in the wearer facing layer than in the garment facing layer.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other fiber materials, such as synthetic, polymeric, or meltblown fibers or with a combination of meltblown and natural fibers. In an embodiment, the cellulosic fluff can include a blend of wood pulp fluff. An example of wood pulp fluff can be "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

The absorbent body 34 can be formed with a dry-forming technique, an air-forming technique, a wet-forming technique, a foam-forming technique, or the like, as well as combinations thereof. A coform nonwoven material may also be employed. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than twenty-four times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 34. In an embodiment, the absorbent body 34 can be free of superabsorbent material. In an embodiment, the absorbent body 34 can have at least about 15% by weight of a superabsorbent material. In an embodiment, the absorbent body 34 can have about 15 to 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 34 can be superposed over the inner layer 62 of the backsheet 26, extending laterally between the leg elastic members, 56, 58, and can be bonded to the inner layer 62 of the backsheet 26, such as by being bonded thereto with adhesive. However, it is to be understood that the absorbent body 34 may be in contact with, and not bonded with, the backsheet 26 and remain within the scope of this disclosure. In an embodiment, the backsheet 26 can be composed of a single layer and the absorbent body 34 can be in contact with the singer layer of the backsheet 26. In an embodiment, a layer, such as but not limited to, a fluid transfer layer 72, can be positioned between the absorbent body 40 and the backsheet 26.

Fluid Transfer Layer:

In various embodiments an absorbent article 10 can be constructed without a fluid transfer layer 72. In various embodiments the absorbent article 10 can have a fluid transfer layer 72. In an embodiment, the fluid transfer layer 72 can be in contact with the absorbent body 34. In an embodiment, the fluid transfer layer 72 can be bonded to the absorbent body 34. Bonding of the fluid transfer layer 72 to the absorbent body 34 can occur via any means known to one of ordinary skill, such as, but not limited to, adhesives. In an embodiment, a fluid transfer layer 72 can be positioned between the body facing liner 28 and the absorbent body 34. In an embodiment, a fluid transfer layer 72 can completely encompass the absorbent body 34 and can be sealed to itself. In such an embodiment, the fluid transfer layer 72 may be folded over on itself and then sealed using, for example, heat and/or pressure. In an embodiment a fluid transfer layer 72 may be composed of separate sheets of material which can be utilized to partially or fully encompass the absorbent body 34 and which can be sealed together using a sealing means such as, but not limited to, an ultrasonic bonder or other thermochemical bonding means or the use of an adhesive.

In an embodiment, the fluid transfer layer 72 can be in contact with and/or bonded with the wearer facing surface 64 of the absorbent body 34. In an embodiment, the fluid transfer layer 72 can be in contact with and/or bonded with the wearer facing surface and at least one of the edges, 36, 38, 40, and/or 42, of the absorbent body 34. In an embodiment, the fluid transfer layer 72 can be in contact with and/or bonded with the body facing surface 34a, at least one of the edges, 36, 38, 40, and/or 42, and the garment facing surface 34b of the absorbent body 34. In an embodiment, the absorbent body 34 may be partially or completely encompassed by a fluid transfer layer 72.

The fluid transfer layer 72 can be pliable, less hydrophilic than the absorbent body 34, and sufficiently porous to thereby permit liquid body exudates to penetrate through the fluid transfer layer 72 to reach the absorbent body 34. In an embodiment, the fluid transfer layer 72 can have sufficient structural integrity to withstand wetting thereof and of the absorbent body 34. In an embodiment, the fluid transfer layer 72 can be constructed from a single layer of material or it may be a laminate constructed from two or more layers of material.

In an embodiment, the fluid transfer layer 72 can include, but is not limited to, natural and synthetic fibers such as, but not limited to, polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers can include, but are not limited to, wool, cotton, flax, hemp, and wood pulp. Wood pulps can include, but are not limited to, standard softwood fluffing grade such as "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

In various embodiments, the fluid transfer layer 72 can include cellulosic material. In various embodiments, the fluid transfer layer 72 can be creped wadding or a high-strength tissue. In various embodiments, the fluid transfer layer 72 can include polymeric material. In an embodiment, a fluid transfer layer 72 can include a spunbond material. In an embodiment, a fluid transfer layer 72 can include a meltblown material. In an embodiment, the fluid transfer layer 72 can be a laminate of a meltblown nonwoven material having fine fibers laminated to at least one spunbond nonwoven material layer having coarse fibers. In such an embodiment, the fluid transfer layer 72 can be a spunbond-meltblown ("SM") material. In an embodiment, the fluid transfer layer 72 can be a spunbond-meltblown-spunbond ("SMS") material. A non-limiting example of such a fluid transfer layer 72 can be a 10 gsm SMS material. In various embodiments, the fluid transfer layer 72 can be composed of at least one material which has been hydraulically entangled into a nonwoven substrate. In various embodiments, the fluid transfer layer 72 can be composed of at least two materials which have been hydraulically entangled into a nonwoven substrate. In various embodiments, the fluid transfer layer 72 can have at least three materials which have been hydraulically entangled into a nonwoven substrate. A non-limiting example of a fluid transfer layer 72 can be a 33 gsm hydraulically entangled substrate. In such an example, the fluid transfer layer 72 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the fluid transfer layer 72 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material.

In various embodiments, a wet strength agent can be included in the fluid transfer layer 72. A non-limiting example of a wet strength agent can be Kymene 6500 (557LK) or equivalent available from Ashland Inc. of Ashland, KY, U.S.A. In various embodiments, a surfactant can be included in the fluid transfer layer 72. In various embodiments, the fluid transfer layer 72 can be hydrophilic. In various embodiments, the fluid transfer layer 72 can be hydrophobic and can be treated in any manner known in the art to be made hydrophilic.

In an embodiment, the fluid transfer layer 72 can be in contact with and/or bonded with an absorbent body 34 which is made at least partially of particulate material such as superabsorbent material. In an embodiment in which the fluid transfer layer 72 at least partially or completely encompasses the absorbent body 34, the fluid transfer layer 72 should not unduly expand or stretch as this might cause the particulate material to escape from the absorbent body 34. In an embodiment, the fluid transfer layer 72, while in a dry state, can have respective extension values at peak load in the machine and cross directions of 30 percent or less and 40 percent or less, respectively.

In an embodiment, the fluid transfer layer 72 can have a longitudinal length the same as, greater than, or less than the longitudinal length of the absorbent body 34. In some embodiments, the fluid transfer layer 72 can have a longitudinal length ranging from about 150 to about 520 mm.

Body Facing Liner:

The body facing liner 28 can have a body facing surface 74 and a garment facing surface 76. In various embodiments, the body facing liner 28 of the absorbent article 10 can overlay the absorbent body 34 and the backsheet 26 and can isolate the wearer's skin from liquid waste retained by the absorbent body 34. In various embodiments, a fluid transfer layer 72 can be positioned between the body facing liner 28 and the absorbent body 34. In various embodiments, an acquisition layer 70 can be positioned between the body facing liner 28 and the absorbent body 34 or a fluid transfer layer 72, if present. In various embodiments, the body facing liner 28 can be bonded to the acquisition layer 70, or to the fluid transfer layer 72 via adhesive and/or by a point fusion bonding. The point fusion bonding may be selected from ultrasonic, thermal, pressure bonding, and combinations thereof.

In an embodiment, the body facing liner 28 can extend beyond the absorbent body 34 and/or a fluid transfer layer 72, and/or an acquisition layer 70 to overlay a portion of the backsheet 26 and can be bonded thereto by any method deemed suitable, such as, for example, by being bonded thereto by adhesive, to substantially enclose the absorbent body 34 between the backsheet 26 and the body facing liner 28. The body facing liner 28 may be narrower than the backsheet 26, but it is to be understood that the body facing liner 28 and the backsheet 26 may be of the same dimensions. It is also contemplated that the body facing liner 28 may not extend beyond the absorbent body 34 and/or may not be secured to the backsheet 26. It is further contemplated that the body facing liner 28 may be composed of more than one segment of material. The body facing liner 28 can be of different shapes, including rectangular, hourglass, or any other shape. The body facing liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

Figure 6:
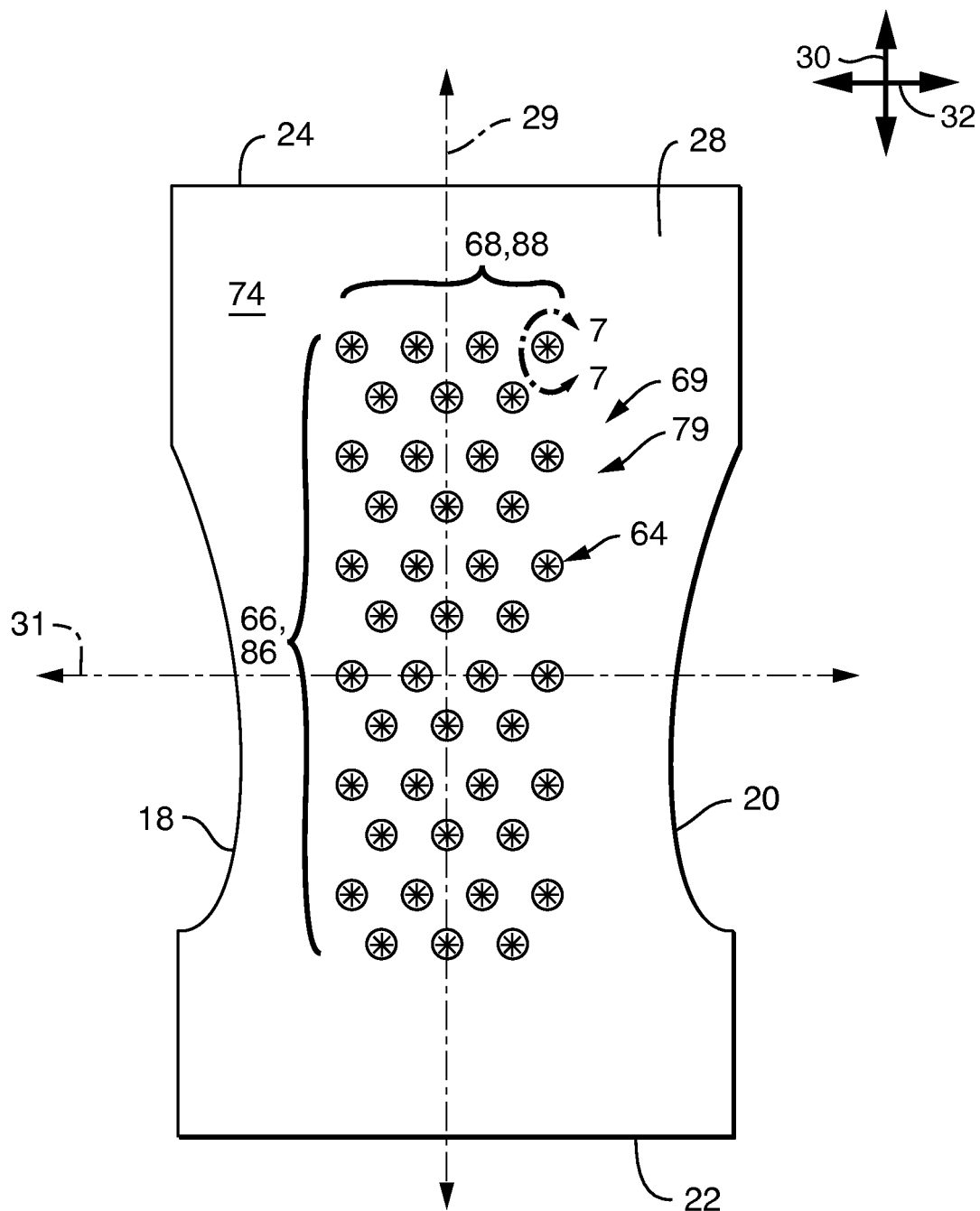
FIG. 6 is a top plan view of an exemplary embodiment of a body facing liner for an absorbent article.
Figure 7:
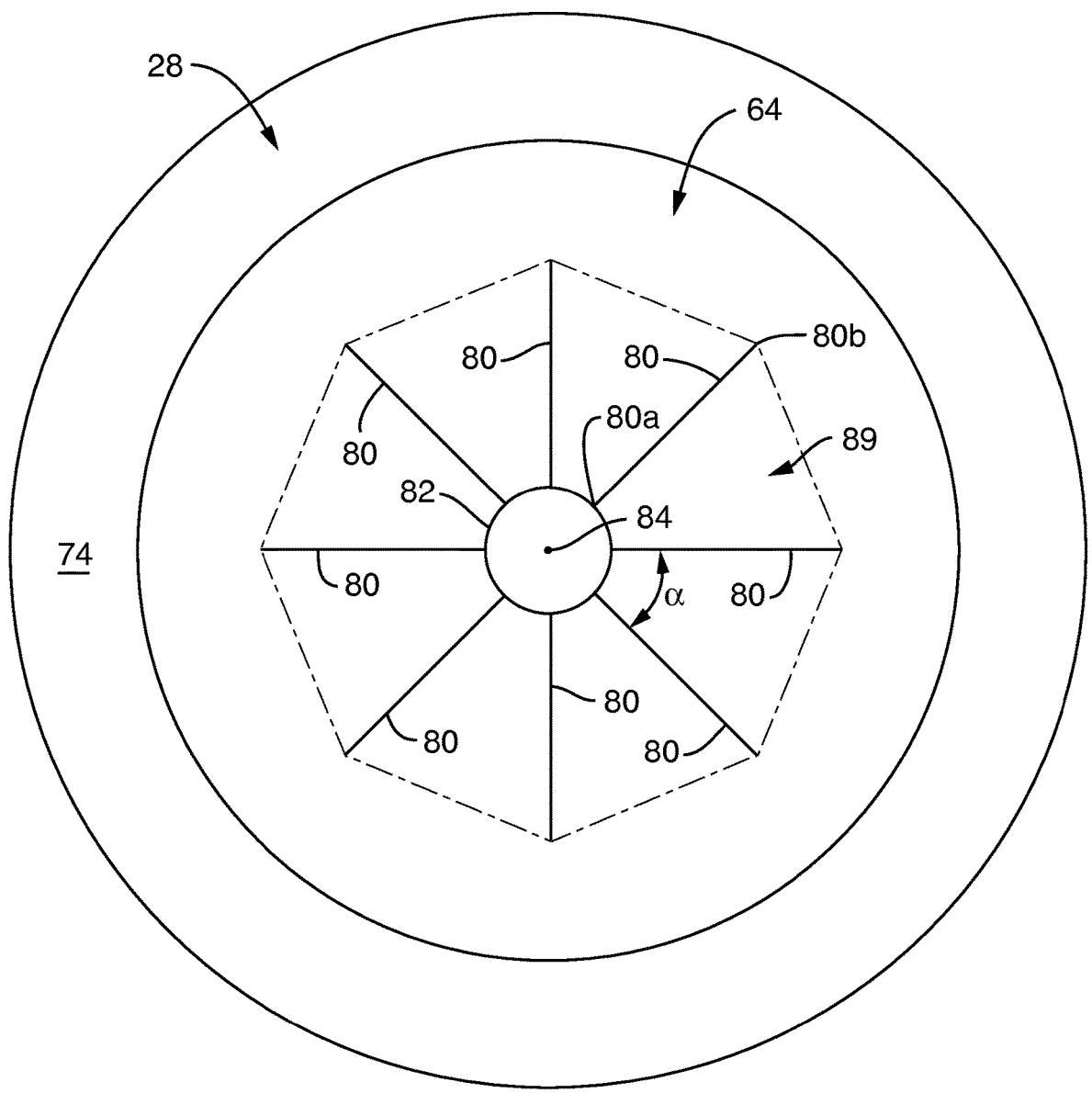
FIG. 7 is a detailed view taken along line 7-7 in FIG. 6.
Figure 12:
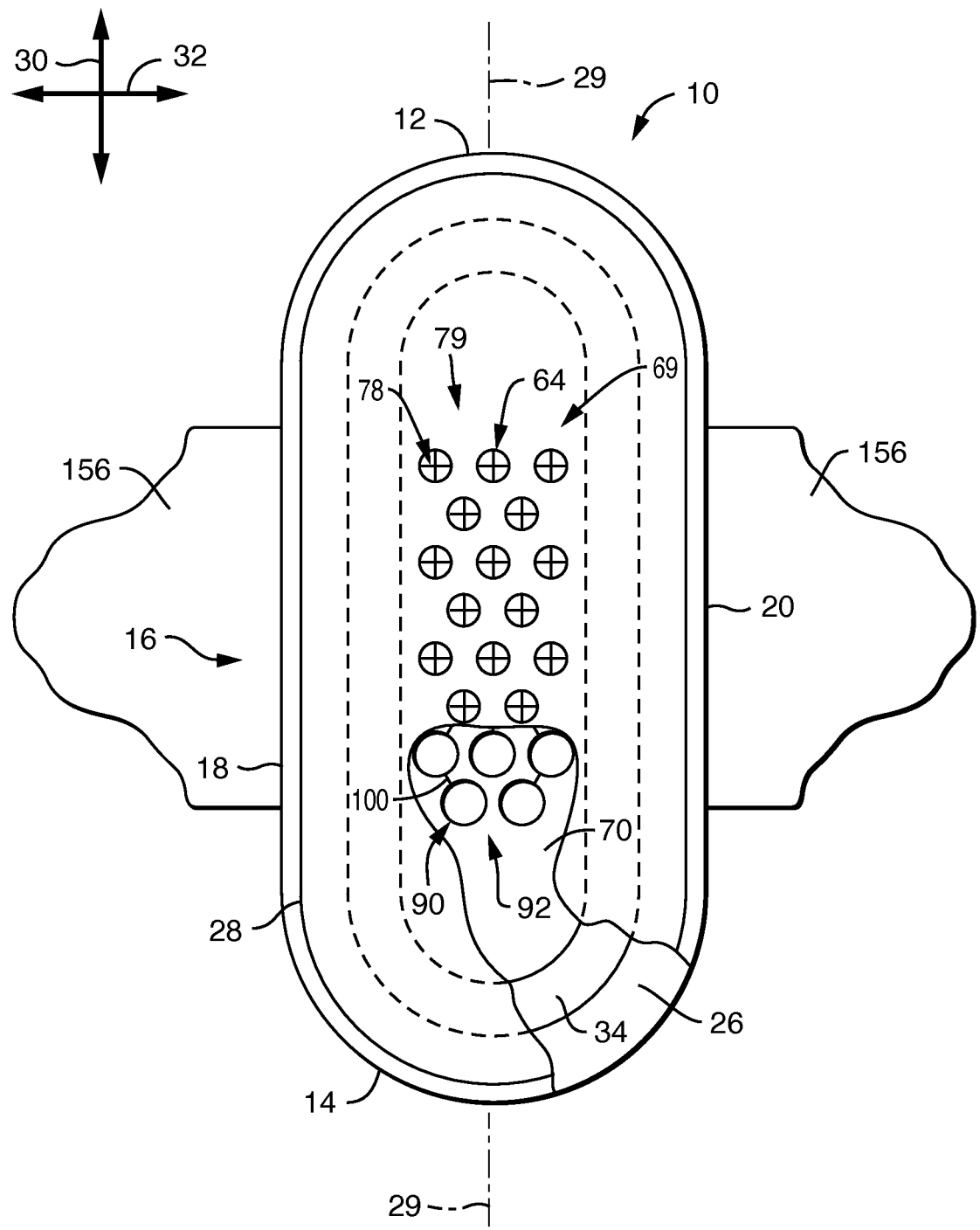
FIG. 12 is a top plan view an exemplary embodiment of an absorbent article, such as a feminine hygiene product.

The body facing liner 28 can include at least one embossment 64. The embossment 64 can provide a three-dimensional structure to the body facing liner 28. In some embodiments, such as the absorbent article 10 illustrated in FIGS. 2 and 6, the body facing liner 28 can include a plurality of embossments 64 (only one embossment 64 being labeled in FIGS. 2 and 6 for purposes of clarity). The embossment 64 can provide a depression in the body facing surface 74 of the body facing liner 28. As viewed from a top plan view, the embossments can be provided in a generally circular nature, such as shown in FIGS. 2, 6, and 7. However, it is contemplated that the embossments 64 can be created in any suitable shape or configuration. The embossments 64 can generally be of the same size within the horizontal plane created by the longitudinal direction 30 and lateral direction 32 (as shown in FIGS. 2, 6, and 12). For example, if an embossment 64 is circular in nature in such a two-dimensional plane, the diameter of the embossment 64 can range from about 3.0 mm to about 50.0 mm. More preferably, the diameter of the embossment 64 can range from about 5.0 mm to about 20.0 mm. Of course, it is contemplated that the diameter of the embossment 64 can be outside of these exemplary ranges.

As illustrated in FIG. 3, each of the embossments 64 can include a depth 65. For purposes herein, the depth 65 of the embossment 64 is defined in the vertical direction 33, which is perpendicular to the plane created by the longitudinal direction 30 and the lateral direction 32, between the body facing surface 74 of the body facing liner 28 at a position 74a that doesn't include an embossment 64 and the body facing surface 74 of the body facing liner 28 at a position 74b forming the lowest point of the embossment 64. In some embodiments, the depth 65 of an embossment 64 can be between about 0.5 mm to about 20.0 mm. More preferably, the depth 65 of an embossment 64 can be between about 1.0 mm to about 10.0 mm, and even more preferably, between about 2.0 mm to about 5.0 mm. It is contemplated that embossments 64 can be provided with a depth 65 outside of these exemplary ranges and still be within the scope of the disclosure. In some embodiments, the depth 65 of each embossment 64 in the body facing liner 28 can be configured to be approximately equal. In some embodiments, however, it is contemplated that some embossments 64 can include a depth 65 that is different from the depth 65 of other embossments 64.

The embossments 64 can be configured into a pattern 69 of rows 66 of embossments 64 and columns 68 of embossments 64, as illustrated in the exemplary embodiment of a body facing liner 28 in FIG. 6. The rows 66 of the embossments 64 can extend in a direction parallel to the lateral axis 31 and can be offset from one another in a direction parallel to longitudinal axis 29. The columns 68 of the embossments 64 can extend in a direction parallel to the longitudinal axis 29 and can be offset from one another in a direction parallel to the lateral axis 31. Of course, it is contemplated that the rows 66 and columns 68 are not limited to such orientations. In an embodiment, the number of rows 66 of embossments 64 can be selected from the range of 1-50, preferably from the range of 4-30, and more preferably from the range of 6-20. In one embodiment, the number of columns 68 of embossments 64 can be selected from the range of 1-25, preferably from the range of 2-20, and more preferably from the range of 3-15. As one exemplary embodiment depicted in FIG. 6 shows, the body facing liner 28 can include twelve rows 66 of embossments 64 and seven columns 68 of embossments 64. As shown in FIG. 6, each row 66 of embossments 64 need not have the same amount of embossments 64 and each column 68 of embossments 64 need not have the same amount of embossments 64. The pattern 69 of embossments 64 depicted in the exemplary embodiment of FIG. 6 has some rows 66 that include four embossments 64 and some rows 66 that include three embossments 64. Although each column 68 of embossments 64 in the embodiment shown in FIG. 6 includes six embossments 64, a pattern 69 of embossments 64 could include one or more columns 68 that have different amounts of embossments 64.

The embossments 64 can help provide a temporary storage mechanism on the body facing surface 74 of the body facing liner 28 for body exudates. In particular, this can be beneficial for urine, menses, and low viscosity fecal matter, which can be prevalent in young children. By containing the body exudates in the embossments 64, the embossments 64 can help prevent body exudates from leaking from the absorbent article 10 by running along the body facing surface 74 of the body facing liner 28. The embossments 64 can also provide the benefit of temporarily storing the body exudates to allow for the rest of the absorbent structure, including the acquisition layer 70, the fluid transfer layer 72, and the absorbent body 34, to intake the liquid body exudates.

The embossments 64 can provide further benefits of increasing the skin comfort of the wearer. For example, by pooling body exudates into the depth 65 of the embossments 64 and away from a position 74a of the body facing surface 74 of the body facing liner 28 that may be in contact with the wearer's skin, the embossments 64 can help reduce irritability of the wearer's skin due to contact with body exudates. Additionally, even when the absorbent article 10 has not been insulted with body exudates, the embossments 64 can reduce the surface area of contact of the body facing surface 74 of the body facing liner 28 to the wearer's skin.

In some embodiments, the body facing liner 28 can include at least one intersecting slit formation 78. The body facing liner 28 can include a plurality of intersecting slit formations 78, as best shown in FIG. 6. The various characteristics of the intersecting slit formations 78 are described herein when the absorbent article 10 is in a stretched, laid flat configuration, such as that shown in FIG. 2. If the body facing liner 28 includes a plurality of intersecting slit formations 78, the intersecting slit formations 78 can be designed to form a pattern 79 on the body facing liner 28 (as best illustrated in FIG. 6). The pattern 79 can be rectangular in shape, hourglass in shape, circular, elliptical, polygonal, or any other desired shape. The pattern 79 of intersecting slit formations 78 can extend throughout the body facing liner 28, from longitudinal side edge 18 to longitudinal side edge 20 and from front waist edge 22 to rear waist edge 24. Alternatively, the pattern 79 of intersecting slit formations 78 can be concentrated such that the pattern 79 does not extend to one or more longitudinal side edge 18, 20 and one or more waist edge 22, 24, as shown in FIG. 2 and FIG. 6. Alternatively, the plurality of intersecting slit formations 78 can form no repeated pattern at all, and be located randomly on the body facing liner 28.

As shown in the detailed view of FIG. 7 depicting one exemplary embodiment of an intersecting slit formation 78 from the body facing liner 28 of FIG. 6, the intersecting slit formation 78 can include at least two intersecting slits 80 and an aperture 82. As shown in FIG. 3, the intersecting slits 80 of the intersecting slit formation 78 can extend from a body facing surface 74 of the body facing liner 28 to the garment facing surface 76 of the body facing liner 28. The intersecting slit formation 78 can be designed such that all of the intersecting slits 80 in the intersecting slit formation 78 extend from the body facing surface 74 to the garment facing surface 76 of the body facing liner 28. In other words, all of the intersecting slits 80 can extend completely through a depth of the body facing liner 28. In other embodiments, some slits 80 of the intersecting slit formation 78 need not extend completely through the body facing liner 28. For example, at least two of the intersecting slits 80 could extend from the body facing surface 74 of the body facing liner 28 to the garment facing surface 76 of the body facing liner 28, yet other slits 80 could extend from the body facing surface 74 of the body facing liner 28 only partially through to the garment facing surface 76 of the body facing liner 28.

The intersecting slit formation 78 shown in FIG. 7 includes eight intersecting slits 80. It is contemplated that a body facing liner 28 could have an intersecting slit formation 78 with a specified amount of intersecting slits 80 selected from the range of 2-20 intersecting slits 80, more preferably from the range of 3-15 intersecting slits 80, and yet more preferably from the range of 3-8 intersecting slits 80. The intersecting slits 80 can intersect at a common intersection point 84, which can be within the aperture 82, if one is present in the intersecting slit formation 78.

The intersecting slits 80 are shown as linear segments, however, the intersecting slits 80 could be arcuate, sinusoidal, or in any other form or shape. An intersecting slit 80 can include a proximal end 80a and a distal end 80b, as labeled on only one of the slits 80 in FIG. 7 for clarity. A linear distance between the proximal end 80a and the distal end 80b can define a length of an intersecting slit 80. The intersecting slits 80 of the intersecting slit formation 78 can each be of the same length as depicted in FIG. 7, however, the intersecting slits 80 of the intersecting slit formation 78 can be of different lengths in comparison to one another. An intersecting slit 80 can be of a specified length selected from a range, including, but not limited to, 2-100 mm, more preferably 2-25 mm, even more preferably, 3-15 mm, and most preferably 4-6 mm. Additionally, the thickness of an exemplary intersecting slit 80 can be selected from the range of 0.02-5.00 mm, more preferably from the range of 0.05-2.00 mm, and even more preferably from the range of 0.10-1.50 mm. In a particular embodiment, the thickness of an intersecting slit 80 can be about 0.20 mm. It can be appreciated, however, that the specified length and thickness of a slit 80 can deviate from the preferred ranges and still be within the scope of this disclosure. It is also contemplated that the thickness of a slit 80 in a body facing liner 28 material in the absorbent article 10 in a stretched, laid flat configuration can vary as compared to the thickness of a slit 80 in a body facing liner 28 during or prior to the manufacturing of the absorbent article 10, due to considerations including, but not limited to, stretch in the body facing liner 28. However, as previously noted, the measurements of the characteristics of the intersecting slit formations 78 described herein are measured when the absorbent article 10 is in a stretched, laid flat configuration, such as that shown in FIG. 2.

Individual intersecting slits 80 can be evenly spaced from one another in angular fashion such that an angle α between consecutive slits 80 is equal between all consecutive intersecting slits 80 in an intersecting slit formation 78. For example, in the embodiment depicted in FIG. 7, the angle α can be equal to about 45°. However, it is contemplated that the intersecting slits 80 need not be evenly spaced from one another in an angular fashion in an intersecting slit formation 78. In one embodiment, where the length of slits 80 in an intersecting slit formation 78 varies, an angle α between adjacent slits 80 can be selected such that the area of material between one pair of adjacent slits 80 and a linear segment extending between the distal ends 80b of those adjacent slits 80 will be approximately equal to the area of material between other adjacent pairs of slits 80.

As mentioned above, an intersecting slit formation 78 can include an aperture 82. The aperture 82 of the intersecting slit formation 78 can be circular in shape, however, similar to the shape of the intersecting slits 80 discussed above, the aperture 82 can be a different shape, including, but not limited to, elliptical, polygonal (triangular, rectangular, etc. . . . ), or irregularly shaped. The aperture 82 can be of various dimensions. For example, a circular shaped aperture 82 as depicted in FIG. 7 can have a diameter selected from the range of 0.5-10.0 mm, more preferably from the range of 0.8-7.0 mm, and even more preferably from the range of 0.9-2.5 mm. In a particular embodiment, a circular shaped aperture 82 can have a diameter of about 1.2 mm. Of course, an aperture 82 can be sized such that it is outside these exemplary ranges and still be within the scope of this disclosure.

As illustrated in FIGS. 2 and 6, one or more of the embossments 64 in the body facing liner 28 can include an intersecting slit formation 78. In some embodiments, the body facing liner 28 can include a plurality of embossments 64 that each include an intersecting slit formation 78. In some embodiments, some embossments 64 in the body facing liner 28 need not include any intersecting slit formation 78. Although not depicted herein, in various embodiments, one or more intersecting slit formations 78 can be located outside of any embossment 64 on the body facing liner 28, or not within any embossment 64.

As illustrated in the detailed view of one embossment 64 and a respective intersecting slit formation 78 in FIG. 7, the embossment 64 and the respective intersecting slit formation 78 can be configured such that the intersecting slit formation 78 is completely disposed within the embossment 64. It is contemplated, however, that in some configurations at least a portion of an intersecting slit formation 78 can extend beyond the embossment 64. For example, a portion of one or more intersecting slits 80 can extend beyond the depression created by the embossment 64.

As previously mentioned, the plurality of intersecting slit formations 78 can be designed to form a pattern 79. In some embodiments, the pattern 79 of intersecting slit formations 78 can be configured to match the pattern 69 of embossments 64 in the body facing liner 28. For example, in some embodiments, the pattern 79 of intersecting slit formations 78 can include a series of rows 86 of intersecting slit formations 78 and a series of columns 88 of intersecting slit formations 78 as depicted in FIG. 6. The rows 86 of the intersecting slit formations 78 can extend in a direction parallel to the lateral axis 31 and can be offset from one another in a direction parallel to longitudinal axis 29. The columns 88 of the intersecting slit formations 78 can extend in a direction parallel to the longitudinal axis 29 and can be offset from one another in a direction parallel to the lateral axis 31. Of course, it is contemplated that the rows 86 and columns 88 are not limited to such orientations. In an embodiment, the number of rows 86 of intersecting slit formations 78 can be selected from the range of 1-50, preferably from the range of 4-30, and more preferably from the range of 6-20. In one embodiment, the number of columns 88 of intersecting slit formations 78 can be selected from the range of 1-25, preferably from the range of 2-20, and more preferably from the range of 3-15. As one exemplary embodiment depicted in FIG. 6 shows, the body facing liner 28 can include twelve rows 86 of intersecting slit formations 78 and seven columns 88 of intersecting slit formations 78. As shown in FIG. 6, each row 86 of intersecting slit formations 78 need not have the same amount of intersecting slit formations 78 and each column 88 of intersecting slit formations 78 need not have the same amount of intersecting slit formations 78. The pattern 79 of intersecting slit formations 78 depicted in the exemplary embodiment of FIG. 6 has some rows 86 that include four intersecting slit formations 78 and some rows 86 that include three intersecting slit formations 78. Although each column 88 of intersecting slit formations 78 in the embodiment shown in FIG. 6 includes six intersecting slit formations 78, a pattern 79 of intersecting slit formations 78 could include one or more columns 88 that have different amounts of intersecting slit formations 78.

FIG. 7 also illustrates the potential open area 89 for an intersecting slit formation 78. The dash-dot-dash broken line in FIG. 7 provides for the potential open area 89 for the respective intersecting slit formation 78. As shown in FIG. 7, the potential open area 89 is configured by constructing a perimeter around the intersecting slit formation 78 by connecting the distal end 80*b* of each successive slit 80 with a linear segment, with only one of the distal ends 80*b* being labeled in FIG. 7 for clarity purposes. The potential open area 89 of an intersecting slit formation 78 can approximate the potential area in the plane of the body facing liner 28 for a particular intersecting slit formation 78 that can allow fluid and/or particulate exudates to pass from a body facing surface 74 of the body facing liner 28 to the garment facing surface 76 of the body facing liner 28 without having to physically pass through the body facing liner 28 material itself. A sum of the total potential open areas 89 of each intersecting slit formation 78 of a pattern 79 can define a total potential open area of the body facing liner 28. In some embodiments, the total potential open area 89 can be between about 1% to about 70% of the total area of the body facing liner 28, more preferably can be between about 3% to about 50% of the total area of the body facing liner 28, even more preferably can be between about 10% to about 40% of the total area of the body facing liner 28, and most preferably can be between about 20% to about 30% of the total area of the body facing liner 28. The benefits of the potential open area 89 of the body facing liner 28 will be explained in further detail below.

The body facing liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the body facing liner 28. The body facing liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The body facing liner 28 need not be a unitary layer structure, and thus, can include more than one layer of fabrics, films, and/or webs, as well as combinations thereof. For example, the body facing liner 28 can include a support layer and a projection layer that can be hydroentangled.

For example, the body facing liner 28 can be composed of a meltblown or spunbond web of polyolefin fibers. Alternatively, the body facing liner 28 can be a bonded-carded web composed of natural and/or synthetic fibers. The body facing liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire body facing liner 28 or it can be selectively applied to particular sections of the body facing liner 28.

In an embodiment, a body facing liner 28 can be constructed of a non-woven bicomponent web. The non-woven bicomponent web can be a spunbonded bicomponent web, or a bonded-carded bicomponent web, or a hydroentangled bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a body facing liner 28 can be a spunbond substrate with a basis weight from about 10 or 12 to about 15 or 20 gsm. In an embodiment, a body facing liner 28 can be a 12 gsm spunbond-meltblown-spunbond substrate having 10% meltblown content applied between the two spunbond layers. In another embodiment, the body facing liner 28 can be a 20 gsm bonded carded web having 50% two denier polyethylene/polyester bicomponent staple fibers and 50% two denier polyethylene/polypropylene bicomponent staple fibers. In other embodiments, the body facing liner 28 can be or can include a thermoplastic film. In some embodiments, the body facing liner 28 can be elastomeric, for example, the body facing liner 28 can include an elastomeric thermoplastic film in some embodiments.

Although the backsheet 26 and body facing liner 28 can include elastomeric materials, it is contemplated that the backsheet 26 and the body facing liner 28 can be composed of materials which are generally non-elastomeric. In an embodiment, the body facing liner 28 can be stretchable, and more suitably elastic. In an embodiment, the body facing liner 28 can be suitably stretchable and more suitably elastic in at least the lateral or circumferential direction of the absorbent article 10. In other aspects, the body facing liner 28 can be stretchable, and more suitably elastic, in both the lateral and the longitudinal directions 32, 30, respectively.

The embossments 64 and the intersecting slit formations 78 can be formed in the body facing liner 28 using various manufacturing techniques. The pattern 69 of embossments 64 can be formed by embossing the body facing liner 28 with embossing rolls. The pattern 79 of intersecting slit formations 78 can be cut into the body facing liner 28 by a rotary die (not shown), a laser cutter (not shown), a water cutter (not shown), or a punch press (not shown). The creation of the embossments 64 and/or the intersecting slit formations 78 can be done off the machine line forming absorbent articles 10, or can be done in-line with the machine line forming absorbent articles 10.

Figure 5:
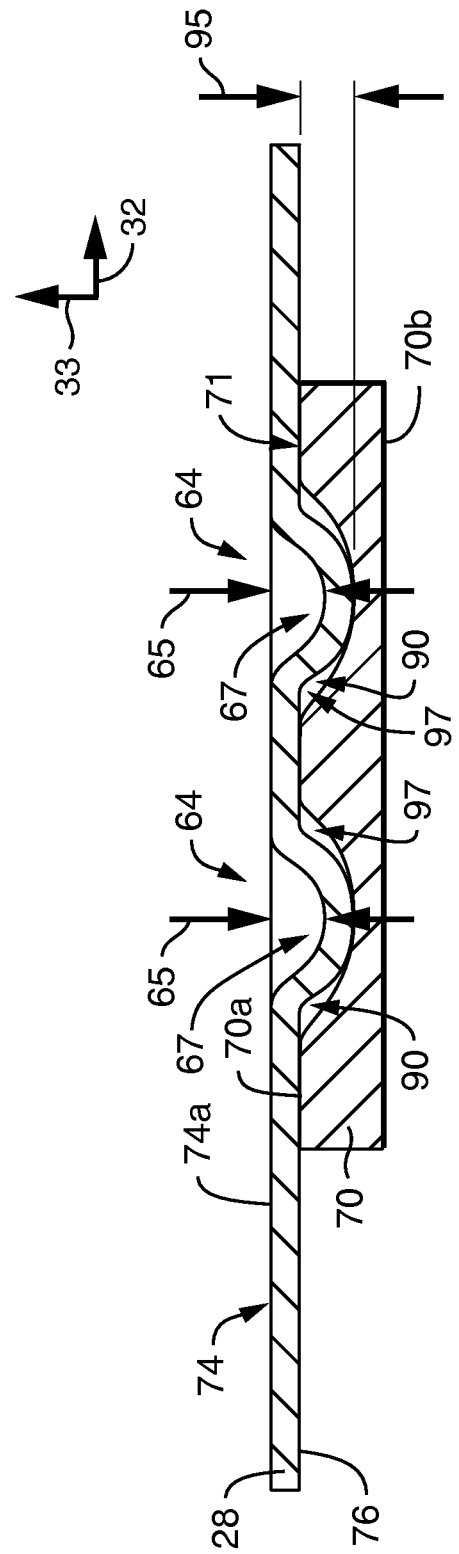
FIG. 5 is a cross-section view of similar to FIG. 4A but showing an alternative embodiment of an acquisition layer.

Acquisition Layer:

The absorbent article 10 can have an acquisition layer 70, 170, 270, 370, 470. FIGS. 2-4B, 8, and 10A show a first embodiment of an acquisition layer 70, FIGS. 5 and 90 show an alternative embodiment of certain aspects of the acquisition layer 70 of FIGS. 2-4B, 8, and 10A, and FIGS. 10B-11C depict further alternative embodiments of acquisition layers 170, 270, 370, 470, respectively, including more than one layer. It is to be noted that the discussion herein with respect to a certain acquisition layer 70, 170, 270, 370, 470 can be applied to other embodiments of the acquisition layer 70, 170, 270, 370, 470 and still remain within the scope of this disclosure.

The acquisition layer 70, 170, 270, 370, 470 can help decelerate and diffuse insults of liquid body exudates penetrating the body facing liner 28, whether the exudates penetrate through passages 85 (as shown in FIG. 4B) formed by intersecting slit formations 78 (if present) or penetrate through the material of the body facing liner 28 itself. In an embodiment, the acquisition layer 70, 170, 270, 370, 470 can be positioned between the body facing liner 28 and the absorbent body 34 to take in and distribute body exudates for absorption by the absorbent body 34. In an embodiment, the acquisition layer 70, 170, 270, 370, 470 can be positioned between the body facing liner 28 and a fluid transfer layer 72 if a fluid transfer layer 72 is present. The acquisition layer 70, 170, 270, 370, 470 can include a body facing surface 70a and a garment facing surface 70b. The body facing surface 70a can include a generally planar portion 71.

In an embodiment, the acquisition layer 70, 170, 270, 370, 470 can be in contact with and/or bonded with the body facing liner 28. In an embodiment in which the acquisition layer 70, 170, 270, 370, 470 is bonded with the body facing liner 28, bonding of the acquisition layer 70, 170, 270, 370, 470 to the body facing liner 28 can occur through the use of an adhesive and/or point fusion bonding, but is not limited to such methods of bonding. For example, the body facing liner 28 could be bonded to the acquisition layer 70, 170, 270, 370, 470 by hydroentangling the body facing liner 28 with the acquisition layer 70, 170, 270, 370, 470. The point fusion bonding can be selected from, but is not limited to, ultrasonic bonding, pressure bonding, thermal bonding, and combinations thereof. In an embodiment, the point fusion bonding can be provided in any pattern as deemed suitable.

As an example, the body facing liner 28 can be bonded to the acquisition layer 70, 170, 270, 370, 470 at a range of 1%-90%. The percentage of bonding between the body facing liner 28 and the acquisition layer 70, 170, 270, 370, 470 can be measured by calculating the area of bonded material between the body facing liner 28 and the acquisition layer 70, 170, 270, 370, 470 and dividing by the area of overlap between the body facing liner 28 and the acquisition layer 70, 170, 270, 370, 470 as viewed from the vertical direction 33.

The acquisition layer 70, 170, 270, 370, 470 can be rectangular in shape, hourglass in shape, or can be any other shape. The acquisition layer 70, 170, 270, 370, 470 may have any longitudinal length dimension as deemed suitable. In some embodiments, the acquisition layer 70, 170, 270, 370, 470 may have a longitudinal length from about 120 to about 520 mm. In an embodiment, the acquisition layer 70, 170, 270, 370, 470 can have any length such that the acquisition layer 70, 170, 270, 370, 470 can be coterminous with the waist edges, 22 and 24, of the absorbent article 10. In an embodiment, the longitudinal length of the acquisition layer 70, 170, 270, 370, 470 can be the same as the longitudinal length of the absorbent body 34. In such an embodiment the midpoint of the longitudinal length of the acquisition layer 70, 170, 270, 370, 470 can substantially align with the midpoint of the longitudinal length of the absorbent body 34.

In an embodiment, the longitudinal length of the acquisition layer 70, 170, 270, 370, 470 can be shorter than the longitudinal length of the absorbent body 34. In such an embodiment, the acquisition layer 70, 170, 270, 370, 470 may be positioned at any desired location along the longitudinal length of the absorbent body 34. As an example of such an embodiment, the absorbent article 10 may contain a target area where repeated liquid surges typically occur in the absorbent article 10. The particular location of a target area can vary depending on the age and gender of the wearer of the absorbent article 10. For example, males tend to urinate further toward the front waist region 12 of the absorbent article 10 and the target area may be phased forward within the absorbent article 10. For example, the target area for a male wearer may be positioned about 2¾" forward of the longitudinal midpoint of the absorbent body 34 and may have a length of about ±3" and a width of about ±2". The female target area can be located closer to the center of the crotch region 16 of the absorbent article 10. For example, the target area for a female wearer may be positioned about 1" forward of the longitudinal midpoint of the absorbent body 34 and may have a length of about ±3" and a width of about ±2". As a result, the relative longitudinal placement of the acquisition layer 70, 170, 270, 370, 470 within the absorbent article 10 can be selected to best correspond with the target area of either or both categories of wearers.

In an embodiment, the absorbent article 10 may contain a target area centered within the crotch region 16 of the absorbent article 10 with the premise that the absorbent article 10 would be worn by a female wearer. The acquisition layer 70, 170, 270, 370, 470, therefore, may be positioned along the longitudinal length of the absorbent article 10 such that the acquisition layer 70, 170, 270, 370, 470 can be substantially aligned with the target area of the absorbent article 10 intended for a female wearer. Alternatively, the absorbent article 10 may contain a target area positioned between the crotch region 16 and the front waist region 12 of the absorbent article 10 with the premise that the absorbent article 10 would be worn by a male wearer. The acquisition layer 70, 170, 270, 370, 470, therefore, may be positioned along the longitudinal length of the absorbent article 10 such that the acquisition layer 70, 170, 270, 370, 470 can be substantially aligned with the target area of the absorbent article 10 intended for a male wearer.

In an embodiment, the acquisition layer 70, 170, 270, 370, 470 can have a size dimension that is the same size dimension as the target area of the absorbent article 10 or a size dimension greater than the size dimension of the target area of the absorbent article 10. In an embodiment, the acquisition layer 70, 170, 270, 370, 470 can be in contact with and/or bonded with the body facing liner 28 at least partially in the target area of the absorbent article 10. In various embodiments, the acquisition layer 70, 170, 270, 370, 470 can have a longitudinal length shorter than, the same as, or longer than the longitudinal length of the absorbent body 34. In such an embodiment, the acquisition layer 70, 170, 270, 370, 470 may be phased from the front end edge 40 of the absorbent body 34 a distance of from about 15 to about 85 mm.

The acquisition layer 70, 170, 270, 370, 470 may have any width as desired. The acquisition layer 70, 170, 270, 370, 470 may have a width dimension from about 15 mm to about 180 mm. The width of the acquisition layer 70, 170, 270, 370, 470 may vary dependent upon the size and shape of the absorbent article 10 within which the acquisition layer 70 will be placed. The acquisition layer 70, 170, 270, 370, 470 can have a width smaller than, the same as, or larger than the width of the absorbent body 34. Within the crotch region 16 of the absorbent article 10, the acquisition layer 70, 170, 270, 370, 470 can have a width smaller than, the same as, or larger than the width of the absorbent body 34.

Figure 8:
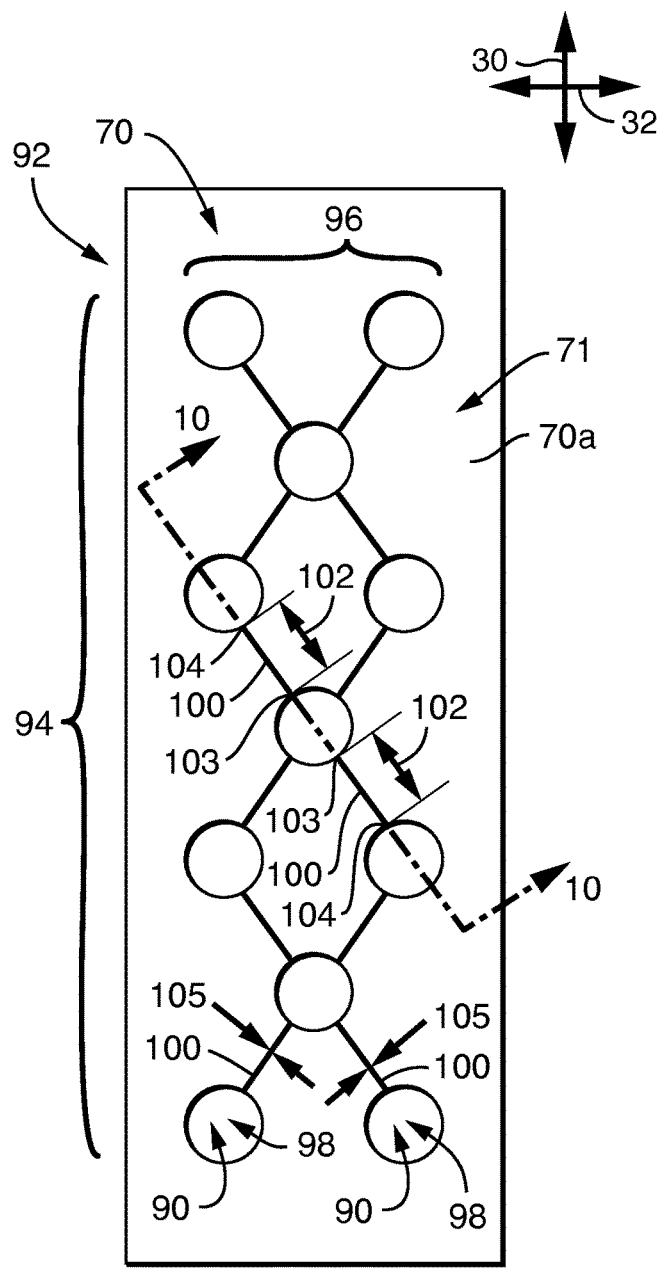
FIG. 8 is a top plan view of an acquisition layer from the absorbent article of FIG. 1.
Figure 9:
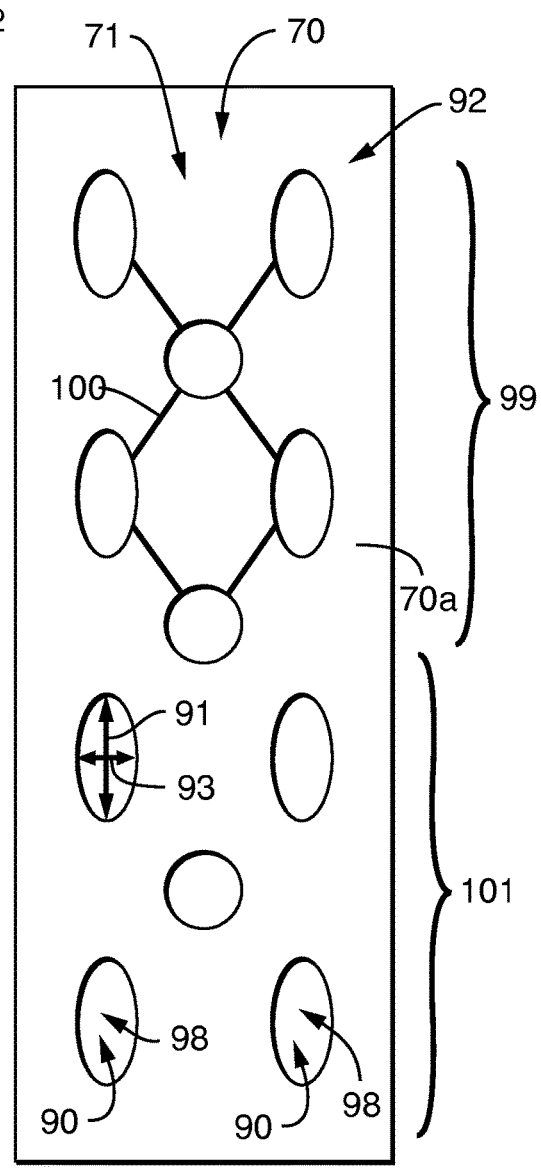
FIG. 9 is a top plan view of an alternative embodiment of an acquisition layer.

In an embodiment, the acquisition layer 70, 170, 270, 370, 470 can have at least one recess 90. FIGS. 8 and 9 provide two exemplary embodiments of an acquisition layer 70 that include a plurality of recesses 90. The proceeding discussion will be with respect to acquisition layer 70, however, can be applied to any other acquisition layer 170, 270, 370, 470 described herein. A recess 90 in the acquisition layer 70 is not considered to be part of the planar portion 71 of the body facing surface 70a of the acquisition layer 70. The plurality of recesses 90 can be in a pattern 92 that form a plurality of rows 94 and a plurality of columns 96. The recesses 90 in the acquisition layer 70 can be of various shapes and sizes in the pattern 92. For example, the recesses 90 can be circular in shape, as shown in the exemplary embodiment in FIGS. 2 and 8. One or more of the recesses 90 can alternatively be elliptical in shape, as illustrated in FIG. 9. As shown in FIG. 8, the acquisition layer 70 can have a pattern 92 of recesses 90 in which all of the recesses 90 are of substantially the same shape. As shown in FIG. 9, the acquisition layer 70 can have a pattern 92 of recesses 90 in which not all of the recesses 90 are of the same shape. Of course, it is contemplated that the recesses 90 in the acquisition layer 70 can be formed in shapes other than circular and elliptical, including, but not limited to, regular and irregular polygons (regular and irregular triangles, regular and irregular rectangles, regular and irregular pentagons, etc. . . . ), and irregular shapes.

The size of the recesses 90 in the acquisition layer 70, 170, 270, 370, 470 can also vary. For example, in an exemplary embodiment, a recess 90 that is circular in shape can have a diameter in the range of about 1.0 mm to about 100.0 mm, preferably in the range of about 4.0 mm to about 50.0 mm, more preferably in the range of about 6.0 mm to about 20.0 mm, and most preferably in the range of about 8.0 mm to about 12.0 mm. In another exemplary embodiment, a recess 90 that is elliptical in shape, such as that shown in FIG. 9, the major axis 91 of the recess 90 can range from about 1.0 mm to about 100.0 mm, preferably in the range of about 4.0 mm to about 50.0 mm, and more preferably in the range of about 6.0 mm to about 20.0 mm. In such an embodiment, the minor axis 93 of a recess 90 that is elliptical in shape can range from about 0.5 mm to about 100.0 mm, preferably in the range of about 0.5 mm to about 45.0 mm, and more preferably in the range of about 3.0 mm to about 15.0 mm. Additionally, although the major axis 91 of the elliptical shaped recesses 90 can be aligned with the longitudinal direction 30 as shown in FIG. 9, the major axis 91 could be designed to be parallel with the lateral direction 32, or form an acute angle with respect to the longitudinal direction 30.

As briefly mentioned above, the pattern 92 of recesses 90 in the acquisition layer 70 can form a plurality of rows 94 and a plurality of columns 96, as shown in FIG. 8. The rows 94 of recesses 90 can extend in a direction parallel to the lateral axis 31 and can be offset from one another in a direction parallel to the longitudinal axis 29. The columns 96 of recesses 90 can extend in a direction parallel to the longitudinal axis 29 and can be offset from one another in a direction parallel to the lateral axis 31. Of course, it is contemplated that the rows 94 and columns 96 of recesses 90 are not limited to such orientations. In an embodiment, the number of rows 94 of recesses 90 can be selected from the range of 1-50, preferably from the range of 4-30, and more preferably from the range of 6-20. In one embodiment, the number of columns 96 of recesses 90 can be selected from the range of 1-25, preferably from the range of 2-20, and more preferably from the range of 3-15. In the exemplary embodiments depicted in FIGS. 8 and 9, the acquisition layer 70 can include seven rows 94 of recesses 90 and three columns 96 of recesses 90. The pattern 92 of recesses 90 depicted in the exemplary embodiments of FIGS. 8 and 9 have some rows 94 that include two recesses 90 and some rows 94 that include one recess 90. In FIGS. 8 and 9, some columns 96 of recesses 90 include four recesses 90 and other columns 96 include three recesses 90, however, it is contemplated that a pattern 92 of recesses 90 could include all of the columns 96 with the same amount of recesses 90.

The recesses 90 can include a depth 95, as labeled in FIG. 3. As will be discussed in further detail below, the recesses 90 can be configured to extend all the way through the acquisition layer 70, 170, 370, 470 from the body facing surface 70a to the garment facing surface 70b of the acquisition layer 70, 170, 370, 470, such as illustrated in FIGS. 3, 4A, 4B, 10A, 10B, 11B, and 110. In such a configuration, the depth 95 of the recesses 90 can be the thickness of the acquisition layer 70, 170, 370, 470 in the vertical direction 33. However in other embodiments, the recesses 90 can be configured to not extend all the way through the acquisition layer 70, 270 from the body facing surface 70a to the garment facing surface 70b of the acquisition layer 70, 270, such as illustrated in FIGS. 5 and 11A. In such a configuration, the depth 95 of the recesses 90 can be some portion of the thickness of the acquisition layer 70, 270 in the vertical direction 33. It is contemplated that the depth 95 of the recesses 90 can vary in an embodiment. As an example, it is contemplated that some of the recesses 90 can be configured to not extend all the way through the acquisition layer 70, 170, 270, 370, 470 from the body facing surface 70a to the garment facing surface 70b of the acquisition layer 70, 170, 270, 370, 470 and other recesses 90 can be configured to extend all the way through the acquisition layer 70, 170, 270, 370, 470 from the body facing surface 70a to the garment facing surface 70b of the acquisition layer 70, 170, 270, 370, 470 within the same acquisition layer 70. In another example, all of the recesses 90 can be configured to not extend all the way through the acquisition layer 70, 170, 270, 370, 470 from the body facing surface 70a to the garment facing surface 70b of the acquisition layer 70, 170, 270, 370, 470, but the depth 95 can vary between different recesses 90.

Each recess 90 in the acquisition layer 70, 170, 270, 370, 470 provides an open area 98 in the acquisition layer 70, 170, 270, 370, 470. The sum of the open areas 98 for each of the plurality of recesses 90 provides a total open area for the acquisition layer 70, 170, 270, 370, 470. In exemplary embodiments, the total open area of the acquisition layer 70, 170, 270, 370, 470 can range from about 1% to about 70% of the total area of the acquisition layer 70, 170, 270, 370, 470, more preferably can range from about 5% to about 45% of the total area of the acquisition layer 70, 170, 270, 370, 470, and even more preferably can range from about 10% to about 40% of the total area of the acquisition layer 70, 170, 270, 370, 470.

The body facing liner 28 and the acquisition layer 70, 170, 270, 370, 470 can be configured such that the embossment 64 or embossments 64 in the body facing liner 28 can be aligned with the recess 90 or recesses 90 in the acquisition layer 70, 170, 270, 370, 470, such as depicted for the acquisition layer 70 as illustrated in FIG. 2. As also shown in FIG. 2, the intersecting slit formation(s) 78 of the body facing liner 28 can be aligned with the recess 90 or recesses 90 of the acquisition layer 70. Furthermore, the design of the pattern 69 of embossments 64 and the design of the pattern 79 of intersecting slit formations 78 in the body facing liner 28 can be aligned and correspond to the pattern 92 of recesses 90 in the acquisition layer 70. For example, the pattern 69 of embossments 64 and the pattern 79 of intersecting slit formations 78 can have the same amount and spacing of rows 66 of embossments 64 and rows 86 of intersecting slit formations 78 as the amount and spacing of rows 94 of recesses 90. Similarly, the pattern 69 of embossments 64 and the pattern 79 of intersecting slit formations 78 can have the same amount and spacing of columns 68 of embossments 64 and columns 88 of intersecting slit formations 78 as the amount and spacing of columns 96 of recesses 90. It is contemplated, however, that in some embodiments not all of the rows 66 and columns 68 of embossments 64 and rows 86 and columns 88 of intersecting slit formations 78 need to be aligned and spaced the same as the rows 94 and columns 96 of recesses 90, but at least some of the rows 66 and columns 68 of embossments 64 and at least some of the rows 86 and columns 88 of intersecting slit formations 78 can be aligned and spaced the same as the rows 94 and columns 96 of recesses 90. In some embodiments, a majority of the rows 66 and columns 68 of embossments 64 and at least a majority of the rows 86 and columns 88 of intersecting slit formations 78 can be aligned and spaced the same as a majority of the rows 94 and columns 96 of recesses 90.

Configuring the body facing liner 28 and the acquisition layer 70, 170, 270, 370, 470 such that the embossment 64 or plurality of embossments 64 in the body facing liner 28 align or correspond to the recess 90 or recesses 90 in the acquisition layer 70 can provide benefits for the absorbent article 10. If one or more intersecting slit formations 78 are present on the body facing liner 28, configuring the body facing liner 28 and the acquisition layer 70, 170, 270, 370, 470 such that the intersecting slit formation(s) 78 align or correspond to the recess 90 or recesses 90 in the acquisition layer 70, 170, 270, 370, 470 can also provide benefits for the absorbent article 10.

For example, referring to FIGS. 3-4B, the embossments 64 of the body facing liner 28 can align and correspond to the recesses 90 of the acquisition layer 70 such that at least some of the embossments 64 of the body facing liner 28 are received by respective recesses 90 in the acquisition layer 70 in a nested configuration. Additionally, the intersecting slit formations 78 can also align and correspond to the recesses 90 of the acquisition layer 70. FIG. 4A depicts the body facing liner 28 and the acquisition layer 70 prior to the absorbent article 10 being subjected to an insult from the wearer, with the embossments 64 being received by the recesses 90 in a nested configuration. The embossments 64 of the body facing liner 28 can at least be partially received by respective recesses 90 in the acquisition layer 70 when in the nested configuration. As illustrated in FIG. 4A, the garment facing surface 76 of the body facing liner 28 at the embossment 64 can be disposed lower than the planar portion 71 of the body facing surface 70a of the acquisition layer 70 (in the vertical direction 33) when the absorbent article 10 is in the stretched, laid flat configuration, such as illustrated in the body facing liner 28 and the acquisition layer of FIGS. 4A-5. As previously noted, the body facing liner 28 and the acquisition layer 70 can be configured such that a plurality of embossments 64 in the body facing liner 28 correspond to and align with a plurality of recesses 90 in the acquisition layer 70. In such a configuration, such as illustrated in FIGS. 3-5, a majority of the plurality of the embossments 64 can be received by respective recesses 90 in a nested configuration as described above with respect to FIGS. 3 and 4A.

In some embodiments, such as the embodiment depicted in FIGS. 3-4B, the depth 65 of the embossments 64 in the body facing liner 28 can be less than the depth 95 of the recesses 90 in the acquisition layer 70. In such a configuration, the embossments 64 can be fully received by the respective recesses 90 in the acquisition layer 70. Whether the embossments 64 in the body facing liner 28 are at least partially received or fully received by the recesses 90 in the acquisition layer 70, the recesses 90 can protect the three dimensional nature that the embossments 64 provide to the body facing liner 28. The acquisition layer 70 can provide beneficial protection for the three dimensional nature of the embossments 64 of the body facing liner 28 in comparison to other components of the absorbent structure, such as the absorbent body 34, due to the properties of the acquisition layer 70. For example, the acquisition layer 70 can comprise thermally bonded fibers that provide bulk and rigidity to the acquisition layer 70. Such bulk and rigidity can provide enhanced protection for the three dimensional nature of the embossments 64 in the body facing liner 28 when the embossments 64 are received in recesses 90 in a nested configuration as described herein.

In one exemplary embodiment, the acquisition layer 70 can be a 30 gsm through air bonded carded web made with eccentric 5 denier polyethylene/polyester bicomponent staple fibers. In another embodiment, the acquisition layer 70 can be a 65 gsm through air bonded carded web made with a fiber size gradient to enhance protection of the 3D shape of the embossments 64 in the body facing liner 28. This structure can contain fibers generally near the body facing surface 70a of the acquisition layer 70 including a 50/50 blend of large denier fibers such as 15 denier polyester staple fiber and 6 denier polyethylene/polypropylene bicomponent staple fiber, and fibers generally near the garment facing surface 70b of the acquisition layer 70 including small denier fibers such as 3 denier polyethylene/polypropylene bicomponent staple fiber. The larger denier fibers near the body facing surface 70a of the acquisition layer 70 will comprise most of the overall basis weight of the acquisition layer 70 to provide the bulk and rigidity to protect the embossments 64 of the body facing liner 28 received by the recesses 90 in the acquisition layer 70. For example, the larger denier fibers near the body facing surface 70a of the acquisition layer 70 can be account for about 50 of the 65 gsm total basis weight of this fiber size gradient structure.

In other embodiments, the depth 65 of the embossments 64 in the body facing liner 28 can be about equal to the depth 95 of the recesses 90 in the acquisition layer 70, such as illustrated in the alternative embodiment in FIG. 5. In such a configuration, the garment facing surface 76 of the body facing liner 28 at the embossment 64 can be about equal to the positioning of the garment facing surface 70b of the acquisition layer 70 in the recess 90. Such a configuration can provide contact between the garment facing surface 76 of the body facing liner 28 at the embossments 64 with a material below the recess 90, whether that be a portion of the acquisition layer 70, the fluid transfer layer 72 (if present), or the absorbent body 34. Such contact can provide improved transfer of body exudates.

When the absorbent article 10 receives an insult of body exudates from the wearer, the embossments 64 can pool the body exudates into the depth 65 of the embossments 64 and away from a position 74a of the body facing surface 74 of the body facing liner 28 that may be in contact with the wearer's skin, as noted above. This can reduce the area of spread of an insult on the body facing surface 74 of the body facing liner 28. If the body exudates include fecal matter, the embossments 64 can reduce the residual fecal matter on the body facing surface 74 of the body facing liner 28 after an insult of exudates. As a result, skin irritation of the wearer of the absorbent article 10 can also be reduced by this alignment. Additionally, such enhanced properties individually, as well as collectively, can reduce the likelihood of the fluid and/or particulate matter exudates from compromising the gasketing system of the absorbent article 10, such as the containment flaps 44, 46.

Another advantage that can be realized by aligning the embossments 64 of the body facing liner 28 with the recesses 90 in the acquisition layer 70, 170, 270, 370, 470 can include enhanced dispersion of the body exudates through the acquisition layer 70, 170, 270, 370, 470, and in turn, to the absorbent body 34. Because the acquisition layer 70, 170, 270, 370, 470 is configured to distribute body exudates, as opposed to absorb them, the body exudates that may pool or collect in the embossments 64 in the body facing liner 28 can be more effectively spread throughout the acquisition layer 70, 170, 270, 370, 470 and to other components of the absorbent structure, such as the absorbent body 34, as compared to if the recesses 90 were located in an absorbent material, such as the absorbent body 34, which may lead to localized saturation of the absorbent material. By configuring the embossments 64 of the body facing liner 28 to be in a nested configuration with respective recesses 90 in the acquisition layer 70, 170, 270, 370, 470, the absorbent body 34 can be more efficiently utilized, which can assist with providing a more comfortable and dry body facing surface 74 of the body facing liner 28.

Furthermore, in embodiments that include an embossment 64 that includes an intersecting slit formation 78, or a plurality of embossments 64 that include an intersecting slit formation 78, the intersecting slit formation 78 can open to provide a passage 85 for body exudates to more quickly and/or effectively pass to other layers or components of the absorbent article 10, including the acquisition layer 70, 170, 270, 370, 470, the fluid transfer layer 72 (if present), and/or the absorbent body 34. The intersecting slit formation 78 can open to provide a passage 85 by displacement of the intersecting slits 80, such as illustrated in FIG. 4B, and can be created by the potential open area 89 as discussed above with respect to FIG. 7. The opening of the intersecting slit formation 78 to provide the passage 85 can provide less resistance to the insult of exudates as they travel from the body facing liner 28 to other layers or components of the absorbent article 10 to increase the efficiency and speed of the intake and distribution of an insult of a fluid and/or particulate matter exudates, further enhancing the benefits noted above with respect to reducing the area of spread of an insult of body exudates and reduce the residual body exudates, such as fecal matter, on the body facing surface 74 of the body facing liner 28. However, as previously mentioned, in some embodiments none of the embossments 64 of the body facing liner 28 can include an intersecting slit formation 78. For example, FIG. 5 discussed above depicts an exemplary embodiment of a body facing liner 28 that includes embossments 64 that do not have an intersecting slit formation 78.

In embodiments that have an embossment 64 that includes an intersecting slit formation 78, the depth 65 of the embossments 64 and the depth 95 of the recesses 90 can be selectively configured to provide benefits for transfer of exudates. As illustrated in FIG. 4B, if the depth 65 of the embossments 64 in the body facing liner 28 are less than the depth 95 of the recesses 90 in the acquisition layer 70, the recesses 90 can provide at least some space in the vertical direction 33 for the intersecting slits 80 of the intersecting slit formations 78 to open to provide a passage 85 with no resistance from underlying material. In some embodiments, the slits 80 of the intersecting slit formations 78 can come into contact with components of the absorbent article 10 under the acquisition layer 70 after the intersecting slit formation 78 opens to provide the passage 85, such as with the fluid transfer layer 72 or the absorbent body 34. Such contact can provide enhanced liquid exudate transfer to the absorbent body 34.

Furthermore, the length of each slit 80 in the intersecting slit formation 78 can be selectively configured based on the difference in depth 65 of the embossments 64 and the depth 95 of the recesses 90. Similar to the discussion above, the depth 65 of the embossments 64 can be less than the depth 95 of the recesses 90. The slits 80 of an intersecting slit formation 78 can be configured such that the slit 80 with the greatest length in the intersecting slit formation 78 can be of a length that is equal to or less than the difference between the depth 65 of the embossments 64 and the depth 95 of the recesses 90. Such a configuration can provide for the intersecting slits 80 of the intersecting slit formation 78 to open to provide the passage 85 without resistance of an underlying material. By way of an example, if the depth 65 of the embossments 64 is five millimeters and the depth 95 of the recesses 90 is ten millimeters, the intersecting slit formation 78 could be configured such that the greatest length of a slit 80 in the intersecting slit formation 78 could be five millimeters or less.

Each embossment 64 in the body facing liner 28 can provide a volume 67 and each recess 90 in the acquisition layer 70 can provide a volume 97, as labeled in FIGS. 4A, 4B, and 5. The volume 67 of the embossment 64 can be selectively configured with the volume 97 of the recess 90 to help provide space to open the intersecting slit formation 78 in the body facing liner 28. In some embodiments, the volume 67 of an embossment 64 in the body facing liner 28 can be less than the volume 97 of a recess 90 in the acquisition layer 70. In some preferred embodiments, the volume 67 of an embossment 64 in the body facing liner 28 can be at least about 10% less than the volume 97 of a recess 90 in the acquisition layer 70. In other preferred embodiments, the volume 67 of an embossment 64 in the body facing liner 28 can be about 10% to about 70% less than the volume 97 of a recess 90 in the acquisition layer 70. Even if the body facing liner 28 is configured without intersecting slit formations 78, the volume 67 of an embossment 64 in the body facing liner 28 being less than the volume 97 of a recess 90 in the acquisition layer 70 can provide additional void volume for the body exudates to temporarily be transferred to and stored in the recess 90 of the acquisition layer 70 before being transferred to other components of the absorbent article 10, such as the absorbent body 34.

The depth 65 of the embossments 64 and the length of the intersecting slits 80 of the intersecting slit formation 78 can also be selectively configured to provide benefits to the body facing liner 28. It can be advantageous to provide the depth 65 of the embossment 64 to be greater than a greatest slit length in the intersecting slit formation 78. Doing so will help prevent pieces of the body facing liner 28 forming the intersecting slit formation 78 from sticking above the depth 65 of the embossment 64 where such pieces of the intersecting slit formation 78 could contact the wearer's skin, in the case where the intersecting slit formation 78 becomes inverted from the position shown in FIG. 4B and extends upwards towards the wearer's skin. More preferably, the depth 65 of the embossment 64 can be at least two times greater than the greatest slit length in the intersecting slit formation 78. For example, if the depth 65 of the embossment 64 is about 8 mm, then it can be advantageous to have the greatest slit length in the intersecting slit formation 78 be about 4 mm. Configuring the depth 65 of the embossments 64 to be greater than the greatest length of the intersecting slit formation 78, and in some embodiments, at least two times greater than the greatest length of the intersecting slit formation 78, can help ensure the body facing surface 74 of the body facing liner 28 provides a soft, smooth surface to be placed against the wearer's skin.

After the fluid and/or particulate matter exudates of an insult passes through the intersecting slit formations 78, at least some of the slits 80 of the intersecting slit formations 78 that created the passage 85 for the insult can fully return, or at least partially return, to their position in the body facing liner 28 as is illustrated in FIG. 4A. This closing, or at least partial closing, of the passages 85 created by the potential open area 89 of each of the intersecting slit formations 78 can reduce the likelihood that fluid and/or particulate matter from an insult can pass from a garment facing surface 76 of the body facing liner 28 to the body facing surface 74 of the body facing liner 28, helping to improve the dryness of the wearer's skin and reduce the likelihood that the fluid and/or particulate matter from an insult may bypass the gasketing system of the absorbent article 10, such as the containment flaps 44, 46. Therefore, the intersecting slit formations 78 can provide more resistance to fluid and/or particulate matter exudates of an insult from flowing back to the wearer than does a body facing liner 28 that has apertures that are similar in quantity to the number of intersecting slit formations 78 and that each provide a similar area, or possibly even a smaller area, as the potential open area 89 of each intersecting slit formation 78.

The tendency of the intersecting slit formations 78 to allow fluid and particulate body exudates to flow from the body facing surface 74 of the body facing liner 28 to the garment facing surface 76 of the body facing liner 28, but not as easily pass from the garment facing surface 76 of the body facing liner 28 back towards the body facing surface 74 of the body facing liner 28 can be further enhanced by the location of intersecting slits 80 of the intersecting slit formation 78 on downward sloping side wall 64a of the embossments 64 (as labeled in FIG. 3). The downward sloping sides 64a of the embossments 64 can open to provide a passage 85 with less resistance when the intersecting slits 80 open towards the acquisition layer 70 as compared to when the intersecting slits 80 open in an opposite orientation away from the acquisition layer 70. This increase in resistance can help provide for the intersecting slit formations 78 helping reduce the possibility of body exudates flowing back to the wearer.

In some embodiments, the acquisition layer 70, 170, 270, 370, 470 can include one or more channels 100, as depicted in FIGS. 2 and 8-12. The acquisition layer 70 illustrated in FIG. 8 includes twelve channels 100, (only four being labeled for clarity purposes). FIG. 10A provides a cross-sectional view taken along line 10-10 from FIG. 8 and illustrates three recesses 90 and two channels 100 that extend between the recesses 90. In some embodiments, at least one recess 90 can be connected to at least two channels 100. As shown in FIG. 8, some recesses 90 can be connected to four channels 100. It is contemplated that in some embodiments, recesses 90 can be connected to more than four channels 100.

Figure 10A:
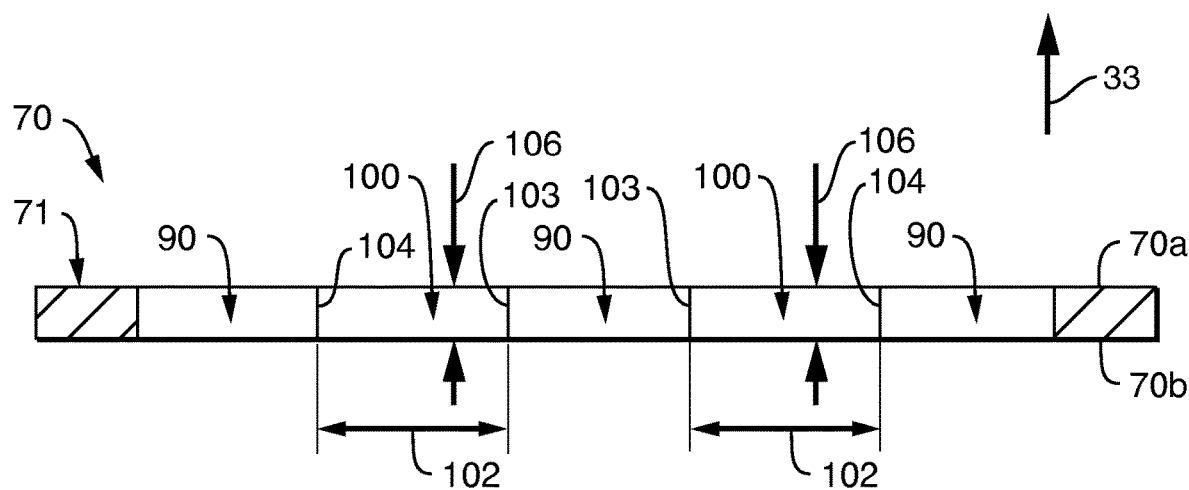
FIG. 10A is a cross-section view of the acquisition layer of FIG. 8 taken along line 10-10.
Figure 11A:
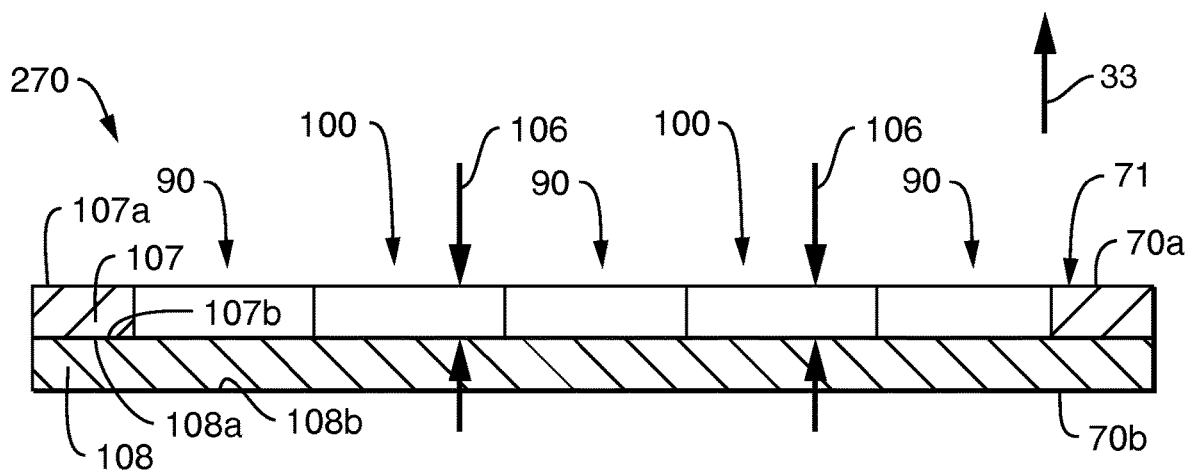
FIG. 11A is a cross-section view of an alternative embodiment of an acquisition layer including two layers.

As shown in FIGS. 8 and 10A, each channel 100 can include a length 102 that is measured in a horizontal plane parallel to the absorbent article 10 when the article 10 is in the stretched, laid flat condition, such as shown in FIG. 2, the horizontal plane including the longitudinal and lateral axes 30, 32, respectively. The length 102 of a channel 100 is defined between a proximal end 103 and a distal end 104 as measured in the horizontal plane discussed above. In some embodiments, the proximal end 103 of a channel 100 can be connected to a recess 90, such as shown in FIG. 10A. In some embodiments, the distal end 104 of the same channel 100 can be connected to a different recess 90 such that the length 102 of the channel 100 extends between, or connects, two recesses 90 of the plurality of recesses 90 in the acquisition layer 70, 170, 270, 370, 470. In some embodiments, a majority of the channels 100 in the acquisition layer 70, 170, 270, 370, 470 can include a proximal end 103 that is connected to at least one recess 90 and a distal end 104 that is connected to a different recess 90. In some embodiments, such as that shown in FIGS. 8 and 9, all of the channels 100 in the acquisition layer 70 can include a proximal end 103 that is connected to at least one recess 90 and a distal end 104 that is connected to a different recess 90. The length 102 of a channel 100 in the acquisition layer 70, 170, 270, 370, 470 can vary, however, in exemplary embodiments, the length 102 of a channel 100 can range between about 1 to about 100 mm, preferably between about 5 to about 30 mm, and more preferably between about 10 to about 20 mm. In some embodiments including more than one channel 100, the length 102 of each channel 100 can be the same for the fluid acquisition layer 70, 170, 270, 370, 470. Although, it is to be noted that the length 102 can vary among different channels 100 in the same fluid acquisition layer 70, 170, 270, 370, 470.

Each channel 100 can also include a thickness 105 measured in the horizontal plane parallel to the absorbent article 10 when the article 10 is in the stretched, laid flat condition. Regardless of the orientation of the channel 100 in the horizontal plane, the length 102 of the channel 100 will be greater than or equal to the thickness 105 of the channel 100. The thickness 105 of a channel 100 in the acquisition layer 70, 170, 270, 370, 470 can vary, however, in exemplary embodiments, the thickness 105 of a channel 100 can range between about 1 to about 30 mm, preferably between about 3 to about 15 mm, and more preferably between about 4 to about 8 mm. In some embodiments including more than one channel 100, the thickness 105 of each channel 100 can be the same for the fluid acquisition layer 70, 170, 270, 370, 470. However, it is to be noted that the thickness 105 can vary among different channels 100 in the same fluid acquisition layer 70, 170, 270, 370, 470.

Figure 10B:
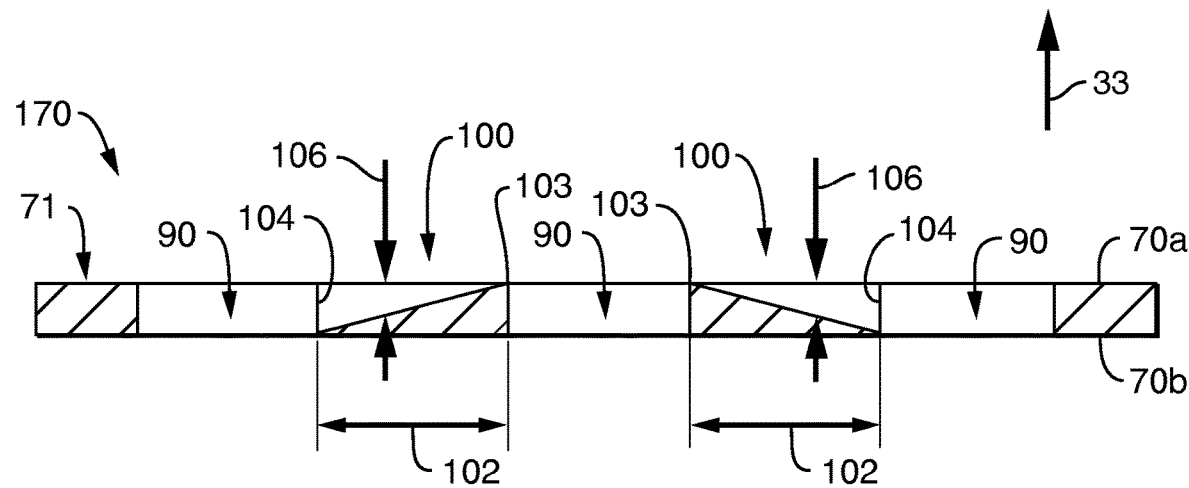
FIG. 10B is a cross-section view of an alternative embodiment of an acquisition layer having channels with varying depth along the length of the channels.

Each channel 100 can also have a depth 106 that is defined in a vertical direction 33. The depth 106 of the channels 100 can extend from the body facing surface 70a of the acquisition layer 70, 170, 270, 370, 470 to the garment facing surface 70b of the acquisition layer 70. As shown in the exemplary embodiment in FIG. 10A, the depth 106 of the channels 100 can be the same along the length 102 of the channels 100. However, in another embodiment of a fluid acquisition layer 170 such as that depicted in FIG. 10B, the depth 106 of a channel 100 can vary along the length 102 of the channel 100. In some embodiments, at the distal end 104 of the channel 100 the depth 106 can extend from the body facing surface 70a of the acquisition layer 170 to the garment facing surface 70b of the acquisition layer 170. As illustrated in FIG. 10B, the depth 106 at the proximal end 103 of the channel 100 can be less than the depth 106 at the distal end 104 of the channel 100. Of course, it is contemplated that the depth 106 at the proximal end 103 of the channel 100 can be greater than the depth 106 at the distal end 104 of the channel 100 in other embodiments, and as such, such a configuration is within the spirit and scope of this disclosure. In some embodiments including more than one channel 100, the depth 106 of each channel 100 can be the same for the fluid acquisition layer 70, 170, 270, 370, 470. It is to be noted that the depth 106 can vary among different channels 100 in the same fluid acquisition layer 70, 170, 270, 370, 470.

The channels 100 in the acquisition layers 70, 170 depicted in the embodiments shown in FIGS. 2 and 8-10B provide advantages in the distribution of the exudates in an absorbent article 10. For example, when exudates transfer through the body facing liner 28 towards the absorbent body 34, the exudates can contact the body facing surface 70a of the acquisition layer 70, 170. The recesses 90 can provide open area 98 in the acquisition layer 70, 170 to accept the exudates and transfer the exudates to other layers of the absorbent article 10, such as a fluid transfer layer 72 (if present) and/or the absorbent body 34. If exudates are concentrated in any particular area of the acquisition layer 70, 170, channels 100 in the acquisition layer 70, 170 can provide reduced resistance in the acquisition layer 70, 170 for the exudates to flow to spread throughout the acquisition layer 70, 170. Such a configuration is believed to increase the effectiveness of distribution of exudates in the acquisition layer 70, 170, especially with semi-solid fecal matter, which may otherwise have difficulty penetrating and spreading throughout the acquisition layer 70, 170. A more effective distribution of the exudates in the acquisition layer 70, 170 can provide an increase in the effectiveness of the absorbent body 34, which in turn can reduce the potential for skin irritation of the wearer by reducing the amount of exudates that may return to the body facing liner 28. Also, the increase in distribution of the exudates throughout the acquisition layer 70, 170 can assist in reducing the likelihood that the gasketing of the absorbent article 10 may be compromised.

Figure 11B:
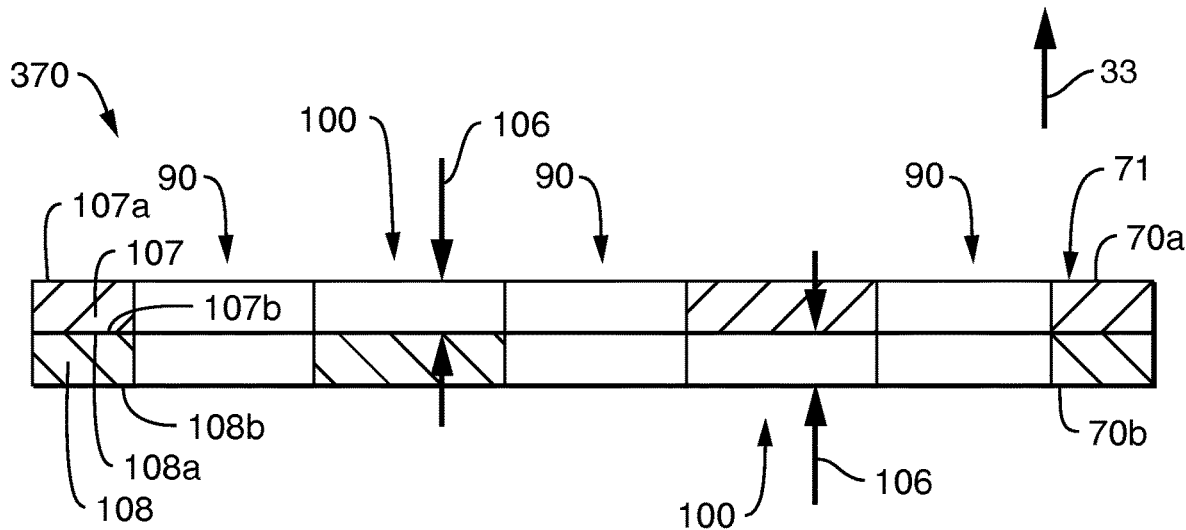
FIG. 11B is a cross-section view of another alternative embodiment of an acquisition layer including two layers.
Figure 11C:
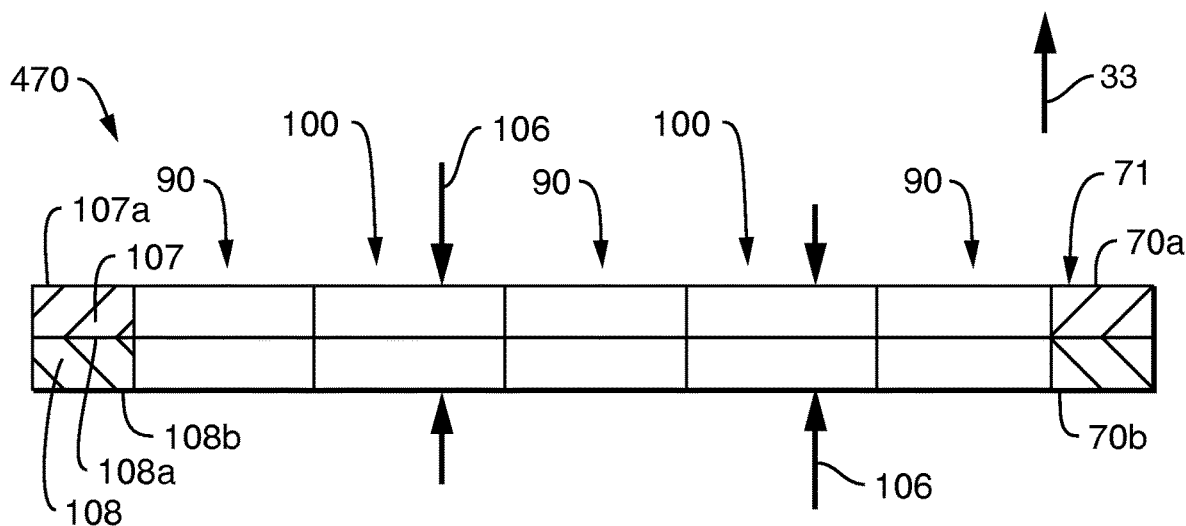
FIG. 11C is a cross-section view of yet another alternative embodiment of an acquisition layer including two layers.

Turning now to FIGS. 11A-11C, alternative embodiments and configurations of fluid acquisition layers 270, 370, 470 that include more than one layer will now be discussed. FIGS. 11A-11C each provides a cross-sectional illustration similar to the cross-sectional illustrations in FIGS. 10A and 10B. FIGS. 11A-11C each depicts fluid acquisition layers 270, 370, 470 that can include a first layer 107 and a second layer 108. A top surface 107a of the first layer 107 can provide the body facing surface 70a of the acquisition layer 270, 370, 470. A bottom surface 108b of the second layer 108 can provide the garment facing surface 70b of the acquisition layer 270, 370, 470. The bottom surface 107b of the first layer 107 can be directly bonded to the top surface 108a of the second layer 108 by adhesives, pressure bonding, ultrasonic bonding, and other suitable methods known by those having ordinary skill in the art.

In the embodiment of the acquisition layer 270 depicted in FIG. 11A, the first layer 107 can include recesses 90 that extend completely through the first layer 107, or from the top surface 107a to the bottom surface 107b of the first layer 107. The first layer 107 can also include channels 100. The channels 100 can extend between the recesses 90, as described above with respect to FIGS. 8-10B. In the embodiment depicted in FIG. 11A, the channels 100 can include a depth 106 that extends from the top surface 107a of the first layer 107 to the bottom surface 107b of the first layer 107. The second layer 108 can be free from recesses 90 and channels 100. Because the second layer 108 does not include any recesses 90 or channels 100, the acquisition layer 270 in FIG. 11A can provide a construction of increased strength. Such a configuration can provide enhanced manufacturability of the acquisition layer 270 when in roll form, while still providing at least some of the benefits noted above with respect to increased effectiveness in distribution of exudates.

FIG. 11B provides yet another alternative embodiment of an acquisition layer 370 that includes a multilayered structure. In FIG. 11B, the acquisition layer 370 can include recesses 90 that extend from the top surface 107a of the first layer 107 to the bottom surface 108b of the second layer 108, or in other words, extend from the body facing surface 70a of the acquisition layer 370 to the garment facing surface 70b of the acquisition layer 370. The first layer 107 can include at least one channel 100 and the second layer 100 can also include at least one channel 100. The channels 100 can extend between the adjacent recesses 90 in the acquisition layer 370, as discussed above. The channel 100 in the first layer 107 can include a depth 106 extending from the top surface 107a of the first layer 107 to the bottom surface 107b of the first layer 107. The channel 100 in the second layer 108 can include a depth 106 extending from the top surface 108a of the second layer 108 to the bottom surface 108b of the second layer 108. Configuring the acquisition layer 370 to include some channels 100 in the first layer 107 and some channels 100 in the second layer 108 can provide an alternative configuration to that as shown in FIG. 11A to help improve the strength of the acquisition layer 370, while still seeking enhanced distribution of exudates in the acquisition layer 370.

FIG. 11C provides yet another alternative embodiment of an acquisition layer 470 that includes more than one layer. In FIG. 11C, the acquisition layer 470 can include recesses 90 that extend from the top surface 107a of the first layer 107 to the bottom surface 108b of the second layer 108, or in other words, extend from the body facing surface 70a of the acquisition layer 470 to the garment facing surface 70b of the acquisition layer 470. The acquisition layer 470 can also include channels 100 extending between the recesses 90. The channels 100 can include a depth 106 extending from the top surface 107a of the first layer 107 to the bottom surface 108b of the second layer 108, or stated differently, from the body facing surface 70a of the acquisition layer 470 to the garment facing surface 70b of the acquisition layer 470.

In the exemplary embodiments depicted in FIGS. 11A-110 and discussed above, the first layer 107 and the second layer 108 of the acquisition layer 270, 370, 470 can be composed of the same material, or can be composed of different materials. In some embodiments, the first layer 107 and/or the second layer 108 can be composed of, but are not limited to, the following materials: fibrous nonwovens such as spunbond webs, meltblown webs and carded webs such as airlaid webs, bonded carded webs, and coform materials; binder and calendar bonded webs; polymer films; nonwoven/polymer film laminates; foams, including open-cell foams; and scrim materials. Various types of wettable, hydrophilic fibers can be used in the first layer 107 and/or the second layer 108. Examples of suitable fibers include, but are not limited to: natural fibers; cellulosic fibers; synthetic fibers composed of cellulose or cellulose derivatives, such as rayon fibers; inorganic fibers composed of an inherently wettable material, such as glass fibers; and synthetic fibers made from inherently wettable thermoplastic polymers, such as particular polyester or polyamide fibers, or nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. In some embodiments, the first layer 107 and/or the second layer 98 can be formed from a material that is substantially hydrophobic, such as a nonwoven web composed of polypropylene, polyethylene, polyester, and the like, and combinations thereof.

Additionally, the first layer 107 and the second layer 108 can have the same or different basis weights. The first layer 107 and the second layer 108 can have the same or different densities. In some embodiments, the second layer 108 can have a greater density than the first layer 107. In some embodiments, the first layer 107 and/or the second layer 108 can include materials having a basis weight ranging from about 10 gsm to about 300 gsm. Furthermore, the first layer 107 and the second layer 108 can include materials having the same or different densities, and the same or different porosities. In some embodiments, the first layer 107 can include fibers of an average denier that is greater than an average denier of fibers in the second layer 108. For example, in some embodiments, the average denier of fibers of the first layer 107 can range from about 5 to about 30 and the average denier of the fibers of the second layer 108 can range from about 1 to about 10. The larger average fiber denier in the first layer 107 can provide enhanced intake of body exudates as compared to the smaller average fiber denier of the second layer 108. Not only can such a fiber denier distribution between first layer 107 and second layer 108 provide enhanced intake of body exudates, but can help prevent flowback of exudates to the body facing liner 28.

Various patterns of channels 100 can exist in the acquisition layer 70, 170, 270, 370, 470. For example, FIG. 9 provides another exemplary embodiment of an acquisition layer 70 where channels 100 only extend between some of the recesses 90 in the acquisition layer 70 (only one channel 100 being labeled in FIG. 9 for clarity purposes). Additionally and/or alternatively, the channels 100 can be located in a channeled region 99 of the acquisition layer 70, and the acquisition layer 70 can include a non-channeled region 101 that can be free from channels 100. The channeled region 99 can be configured to correspond to a portion of the absorbent article 10 more likely to receive exudates in general, or particular forms of exudates. For example, the acquisition layer 70 depicted in FIG. 9 could be configured within an absorbent article 10 such that the channeled region 99 is located near the rear waist region 14 and/or the crotch region 16 which is more likely to be insulted with semi-solid fecal material. Alternatively, the acquisition layer 70 could be configured within an absorbent article 10 such that the channeled region 99 is located near the crotch region 16 and/or the front waist region 12. It is contemplated that this and similar configurations of channels 100 in the acquisition layer 70 as shown in FIG. 9 could be applied to other embodiments of the acquisition layers described above.

In exemplary embodiments, the acquisition layer 70, 170, 270, 370, 470 can include woven materials; fibrous nonwovens such as spunbond webs, meltblown webs and carded webs such as airlaid webs, bonded carded webs, and coform materials; binder and calendar bonded webs; foams, including open-cell foams; and scrim materials. The acquisition layer 70, 170, 270, 370, 470 can include various types of fibers such as natural fibers; cellulosic fibers; synthetic fibers composed of cellulose or cellulose derivatives, such as rayon fibers; inorganic fibers composed of an inherently wettable material, such as glass fibers; and synthetic fibers made from inherently wettable thermoplastic polymers, such as particular polyester or polyamide fibers, or nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. In some embodiments, the acquisition layer 70, 170, 270, 370, 470 can be formed from a material that is substantially hydrophobic, such as a nonwoven web composed of polypropylene, polyethylene, polyester, and the like, and combinations thereof. In some embodiments, the acquisition layer 70, 170, 270, 370, 470 can include materials having a basis weight ranging from about 10 gsm to about 300 gsm. In an embodiment, the acquisition layer 70, 170, 270, 370, 470 can have a basis weight of less than 100 gsm. More preferably, the acquisition layer 70, 170, 270, 370, 470 can have a basis weight of less than 75 gsm, and even more preferably, less than 50 gsm.

The recesses 90 can be formed in the acquisition layer 70, 170, 270, 370, 470 using various manufacturing techniques. For example, a pattern 92 of recesses 90 that extend from the body facing surface 70a to the garment facing surface 70b of the acquisition layer 70 can be cut into the acquisition layer 70 by a rotary die (not shown), a laser cutter (not shown), a water cutter (not shown), or a punch press (not shown). A pattern 92 of recesses 90 that do not extend all the way through the acquisition layer 70 from the body facing surface 70a to the garment facing surface 70b of the acquisition layer 70 can be created by embossing rollers. Channels 100 can also be formed in the acquisition layer 70, 170, 270, 370, 470 in a variety of manufacturing techniques and equipment, including rotary dies, laser cutters, water cutters, punch presses, etc. (not shown).

Containment Flaps:

In an embodiment, containment flaps, 44, 46, can be secured to the body facing liner 28 of the absorbent article 10 in a generally parallel, spaced relation with each other laterally inward of the leg openings to provide a barrier against the flow of body exudates. In an embodiment, the containment flaps, 44, 46, can extend longitudinally from the front waist region 12 of the absorbent article 10, through the crotch region 16 to the back waist region 14 of the absorbent article 10. A proximal end 120 of the containment flaps 44, 46 can be bonded to the body facing liner 28 with a seam of adhesive 122. Alternatively, each containment flap 44, 46 can be bonded to other components of the absorbent article 10 other than the body facing liner 28, including, but not limited to, the backsheet 26.

The containment flaps, 44 and 46, can be constructed of a fibrous material which can be similar to the material forming the body facing liner. Other conventional materials, such as polymer films, can also be employed. Each containment flap, 44 and 46, can have a moveable distal end 124 which can include flap elastics, such as flap elastics 48 and 50, respectively. Suitable elastic materials for the flap elastic, 48 and 50, can include sheets, strands or ribbons of natural rubber, synthetic rubber, or thermoplastic elastomeric materials.

The flap elastics, 48 and 50, as illustrated, can have two strands of elastomeric material extending longitudinally along the distal ends 124 of the containment flaps, 44 and 46, in generally parallel, spaced relation with each other. The elastic strands can be within the containment flaps, 44 and 46, while in an elastically contractible condition such that contraction of the strands gathers and shortens the distal ends 124 of the containment flaps, 44 and 46. As a result, the elastic strands can bias the distal ends 124 of each containment flap, 44 and 46, toward a position spaced from the proximal end 120 of the containment flaps, 44 and 46, so that the containment flaps, 44 and 46, can extend away from the body facing liner 28 in a generally upright orientation of the containment flaps, 44 and 46, especially in the crotch region 16 of the absorbent article 10, when the absorbent article 10 is fitted on the wearer. The distal end 124 of the containment flaps, 44 and 46, can be connected to the flap elastics, 48 and 50, by partially doubling the containment flap, 44 and 46, material back upon itself by an amount which can be sufficient to enclose the flap elastics, 48 and 50. It is to be understood, however, that the containment flaps, 44 and 46, can have any number of strands of elastomeric material and may also be omitted from the absorbent article 10 without departing from the scope of this disclosure.

Leg Elastics:

Leg elastic members 56, 58 can be secured to the backsheet 26, such as by being bonded thereto by laminate adhesive, generally laterally inward of the longitudinal side edges, 18 and 20, of the absorbent article 10. The leg elastic members 56, 58 can form elasticized leg cuffs 57, 59, respectively, that further help to contain body exudates. In an embodiment, the leg elastic members 56, 58 may be disposed between the inner layer 62 and outer layer 60 of the backsheet 26 or between other layers of the absorbent article 10. The leg elastic members 56, 58 can be a single elastic member as illustrated in the figures herein, or each leg elastic member 56, 58 can include more than one elastic member. A wide variety of elastic materials may be used for the leg elastic members 56, 58. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

Fastening System:

In an embodiment, the absorbent article 10 can include a fastener system. The fastener system can include one or more back fasteners 130 and one or more front fasteners 132. Portions of the fastener system may be included in the front waist region 12, back waist region 14, or both. The fastener system can be configured to secure the absorbent article 10 about the waist of the wearer and maintain the absorbent article 10 in place during use. In an embodiment, the back fasteners 130 can include one or more materials bonded together to form a composite ear as is known in the art. For example, the composite fastener may be composed of a stretch component 134, a nonwoven carrier or hook base 136, and a fastening component 138.

Waist Elastic Members:

In an embodiment, the absorbent article 10 can have waist elastic members, 52 and 54, which can be formed of any suitable elastic material. The waist elastic member 52 can be in a rear waist region 14 of the absorbent article 10 and the waist elastic member 54 can be in a front waist region 12 of the absorbent article 10. Suitable elastic materials for the waist elastic members 52, 54 can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 52 and 54, may be omitted from the absorbent article 10 without departing from the scope of this disclosure.

Feminine Hygiene Product:

FIG. 12 provides a non-limiting illustration of an absorbent article 10 in the form of a feminine hygiene product such as a menstrual pad or feminine adult incontinence product. The absorbent article 10 can have a lengthwise, longitudinal direction 30 and a transverse, lateral direction 32. Additionally, the absorbent article 10 can include first and second longitudinally opposed front and rear end regions, 12 and 14 (which can be referred to as front waist regions and rear waist regions, respectively), and an intermediate region (or crotch region) 16, located between the end regions, 12 and 14. The absorbent article 10 can have first and second longitudinal side edges, 18 and 20, which can be the longitudinal sides of the elongated absorbent article 10. The longitudinal side edges, 18 and 20, can be contoured to match the shape of the absorbent article 10. The absorbent article 10 can have any desired shape such as, for example, a dog bone shape, a race track shape, an hourglass shape, or the like. Additionally, the absorbent article 10 can be substantially longitudinally symmetric, or may be longitudinally asymmetric, as desired.

As representatively shown, the longitudinal dimension of the absorbent article 10 can be relatively larger than the transverse lateral dimension of the absorbent article 10.

Configurations of the absorbent article 10 can include a body facing liner 28 and a backsheet 26, such as described herein. An absorbent body 34, such as described herein, can be positioned between the body facing liner 28 and the backsheet 26. As representatively shown, for example, the peripheries of the body facing liner 28 and the backsheet 26 can be substantially entirely coterminous or the peripheries of the body facing material 28 and the backsheet 26 can be partially or entirely non-coterminous. In an embodiment, the absorbent article 10 can include an acquisition layer 70 such as described herein. In other embodiments, the absorbent article 10 can include one of the other variations of an acquisition layer 170, 270, 370, 470 as described herein.

The body facing liner 28 can include a pattern 69 of embossments 64 and a pattern 79 of intersecting slit formations 78, such as described herein. The acquisition layer 70 can include a pattern 92 of recesses 90. The embossments 64 and the intersecting slit formations 78 in the body facing liner 28 can be aligned with the recesses 90 in the acquisition layer 70, as previously described, to provide the advantages for the absorbent article 10 noted above.

In an embodiment in which the absorbent article 10 can be a feminine hygiene product, the absorbent article 10 can include laterally extending wing portions 156 that can be integrally connected to the side edges, 18 and 20, of the absorbent article 10 in the intermediate region 16 of the absorbent article 10. For example, the wing portions 156 may be separately provided members that are subsequently attached or otherwise operatively joined to the intermediate region 16 of the absorbent article 10. In other configurations, the wing portions 156 may be unitarily formed with one or more components of the absorbent article 10. As an example, a wing portion 156 may be formed from a corresponding, operative extension of the body facing liner 28, the backsheet 26, and combinations thereof.

The wing portions 156 can have an appointed storage position (not shown) in which the wing portions 156 are directed generally inwardly toward the longitudinal axis 29. In various embodiments, the wing portion 156 that is connected to one side edge, such as side edge 18, may have sufficient cross-directional length to extend and continue past the axis 29 to approach the laterally opposite side edge 20 of the absorbent article 10. The storage position of the wing portions 156 can ordinarily represent an arrangement observed when the absorbent article 10 is first removed from a wrapper or packaging. Prior to placing the absorbent article 10, such as the feminine hygiene product, into a bodyside of an undergarment prior to use, the wing portions 156 can be selectively arranged to extend laterally from the side edges, 18 and 20, of the absorbent article 10 intermediate region 16. After placing the absorbent article 10 into the undergarment, the wing portions 156 can be operatively wrapped and secured around the side edges 18, 20 of the undergarment to help hold the absorbent article 10 in place, in a manner well known in the art.

The wing portions 156 can have any operative construction and can include a layer of any operative material. Additionally, each wing portion 156 can comprise a composite material. For example, the wing portions 156 can include a spunbond fabric material, a bicomponent spunbond material, a necked spunbond material, a neck-stretched-bonded laminate (NBL) material, a meltblown fabric material, a bonded carded web, a thermal bonded carded web, a through-air bonded carded web, or the like, as well as combinations thereof.

Each wing portion 156 can include a panel-fastener component (not shown) which can be operatively joined to an appointed engagement surface of its associated wing portion 156. The panel-fastener component can include a system of interengaging mechanical fasteners, a system of adhesive fasteners, or the like, as well as combinations thereof. In an embodiment, either or both wing portions 156 can include a panel-fastener system which incorporates an operative adhesive. The adhesive may be a solvent based adhesive, a hot melt adhesive, a pressure-sensitive adhesive, or the like, as well as combinations thereof.

In an embodiment, a garment attachment mechanism (not shown), such as a garment attachment adhesive, can be distributed onto the garment side of the absorbent article 10. In an embodiment, the garment adhesive can be distributed over the garment side of the absorbent article 10 of the backsheet 26, and one or more layers or sheets of release material can be removably placed over the garment adhesive for storage prior to use. In an embodiment, the garment attachment mechanism can include an operative component of a mechanical fastening system. In such an embodiment, the garment attachment mechanism can include an operative component of a hook-and-loop type of fastening system.

Decolorizing Composition:

In an embodiment, a chemical treatment may be employed to alter the color of bodily exudates captured by the absorbent article 10. In an embodiment, for example, the treatment may be a decolorizing composition that agglutinates (agglomerates) red blood cells in blood and menses and limits the extent that the red color of menses is visible. One such composition includes a surfactant, such as described in U.S. Pat. No. 6,350,711 to Potts, et al., which is incorporated herein in its entirety by reference thereto. Non-limiting examples of such surfactants include Pluronic® surfactants (tri-block copolymer surfactant), inorganic salts that contain a polyvalent anion (e.g., divalent, trivalent, etc.), such as sulfate ($SO_4^{2-}$), phosphate ($PO_4^{3-}$), carbonate ($CO_3^{2-}$), oxide ($O^{2-}$), etc., and a monovalent cation, such as sodium ($Na^+$), potassium ($K^+$), lithium ($Li^+$), ammonium ($NH_4^+$), etc. Alkali metal cations are also beneficial. Some examples of salts formed from such ions include, but are not limited to, disodium sulfate ($Na_2SO_4$), dipotassium sulfate ($K_2SO_4$), disodium carbonate ($Na_2CO_3$), dipotassium carbonate ($K_2CO_3$), monosodium phosphate ($NaH_2PO_4$), disodium phosphate ($Na_2HPO_4$), monopotassium phosphate ($KH_2PO_4$), dipotassium phosphate ($K_2HPO_4$), etc. Mixtures of the aforementioned salts may also be effective in facilitating physical separation of red blood cells. For example, a mixture of disodium sulfate ($Na_2SO_4$) and monopotassium phosphate ($KH_2PO_4$) may be employed.

Besides agglutinating agents, the decolorizing composition may alter the chemical structure of hemoglobin to change its color. Examples of such compositions are described in U.S. Patent Application Publication No. 2009/0062764 to MacDonald, et al., which is incorporated herein in its entirety by reference thereto. In an embodiment, the composition can include an oxidizing agent that can be generally capable of oxidizing hemoglobin or other substances responsible for unwanted color of the bodily exudates. Some examples of oxidizing agents include, but are not limited to, peroxygen bleaches (e.g., hydrogen peroxide, percarbonates, persulphates, perborates, peroxyacids, alkyl hydroperoxides, peroxides, diacyl peroxides, ozonides, supereoxides, oxo-ozonides, and periodates); hydroperoxides (e.g., tert-butyl hydroperoxide, cumyl hydroperoxide, 2,4,4-trimethylpentyl-2-hydroperoxide, di-isopropylbenzene-monohydroperoxide, tert-amyl hydroperoxide and 2,5-dimethyl-hexane-2,5-dihydroperoxide); peroxides (e.g., lithium peroxide, sodium peroxide, potassium peroxide, ammonium peroxide, calcium peroxide, rubidium peroxide, cesium peroxide, strontium peroxide, barium peroxide, magnesium peroxide, mercury peroxide, silver peroxide, zirconium peroxide, hafnium peroxide, titanium peroxide, phosphorus peroxide, sulphur peroxide, rhenium peroxide, iron peroxide, cobalt peroxide, and nickel peroxide); perborates (e.g., sodium perborate, potassium perborate, and ammonium perborate); persulphates (e.g., sodium persulphate, potassium dipersulphate, and potassium persulphate); and so forth. Other suitable oxidizing agents include, but are not limited to omega-3 and -6 fatty acids, such as linoleic acids, α-linoleic acid, arachidonic acid, eicosapentaenoic acid, docosahexaenoic acid, eicosadienoic acid, eicosatrienoic acid, etc.

The decolorizing composition may be applied to any liquid permeable layer of the absorbent article 10 where it can contact aqueous fluids exuded by the body, such as, for example, menses, such as the body facing liner 28, acquisition layer 70, fluid transfer layer 72, absorbent body 34, backsheet 26, and combinations thereof. In an embodiment, the decolorizing composition may be applied to only a portion of the surface of the layer(s) to which it is applied to ensure that the layer(s) is still capable of retaining sufficient absorbent properties. In an embodiment, it may be desired that the decolorizing composition is positioned closer to the absorbent body 40. In an embodiment, an additional layer (not shown) may be employed in the absorbent article 10 and may be applied with the decolorizing composition that is in contact with the absorbent body 40. The additional layer may be formed from a variety of different porous materials, such as a perforated film, nonwoven web (e.g., cellulosic web, spunbond web, meltblown web, etc.), foams, etc. In an embodiment, the additional layer may be in the form of a hollow enclosure (e.g., sachet, bag, etc.) that is folded so that it partially or completely surrounds the absorbent body 40. The decolorizing composition may be disposed within this enclosure so that it remains sealed therein prior to use.

EMBODIMENTS

Embodiment 1

An absorbent article including a longitudinal axis and a lateral axis, the absorbent article comprising: a front waist region, a rear waist region, a crotch region, the crotch region being disposed between the front waist region and the rear waist region; a front waist edge in the front waist region, a rear waist edge in the rear waist region, and a first longitudinal side edge and a second longitudinal side edge, the first longitudinal side edge and the second longitudinal side edge each extending from the front waist edge to the rear waist edge; a body facing liner including a body facing surface and a garment facing surface, the body facing liner including at least one embossment; a backsheet; an absorbent body disposed between the body facing liner and the backsheet; and an acquisition layer including a body facing surface and a garment facing surface, the body facing surface of the acquisition layer including a planar portion, the acquisition layer including at least one recess that does not extend from the body facing surface of the acquisition layer to the garment facing surface of the acquisition layer, the at least one recess receiving the at least one embossment of the body facing liner in a nested configuration.

Embodiment 2

An absorbent article including a longitudinal axis and a lateral axis, the absorbent article comprising: a front waist region, a rear waist region, a crotch region, the crotch region being disposed between the front waist region and the rear waist region; a front waist edge in the front waist region, a rear waist edge in the rear waist region, and a first longitudinal side edge and a second longitudinal side edge, the first longitudinal side edge and the second longitudinal side edge each extending from the front waist edge to the rear waist edge; a body facing liner including a body facing surface and a garment facing surface, the body facing liner including at least one embossment, the embossment including an intersecting slit formation; a backsheet; an absorbent body disposed between the body facing liner and the backsheet; and an acquisition layer including a body facing surface and a garment facing surface, the acquisition layer including at least one recess, the at least one recess receiving the at least one embossment of the body facing liner in a nested configuration.

Embodiment 3

The absorbent article of embodiment 1 or embodiment 2, wherein the nested configuration provides that the garment facing surface of the body facing liner at the at least one embossment is disposed lower than the planar portion of the body facing surface of the acquisition layer when the absorbent article in a stretched, laid flat configuration.

Embodiment 4

The absorbent article of embodiment 1, wherein the at least one embossment includes an intersecting slit formation.

Embodiment 5

The absorbent article of any of the preceding embodiments, wherein the body facing liner includes a plurality of embossments and the acquisition layer includes a plurality of recesses, at least some of the plurality of recesses receiving one of the plurality of embossments of the body facing liner in a nested configuration.

Embodiment 6

The absorbent article of embodiment 5, wherein a majority of the plurality of embossments includes an intersecting slit formation.

Embodiment 7

The absorbent article of any one of embodiments 1-4, wherein the at least one embossment includes a first depth and the at least one recess includes a second depth, and wherein the first depth is less than the second depth.

Embodiment 8

The absorbent article of embodiment 5, wherein a majority of the plurality of embossments includes a first depth and a majority of the plurality of recesses includes a second depth, and wherein the first depth is less than the second depth.

Embodiment 9

The absorbent article of embodiment 5, wherein a majority of the plurality of the embossments includes a first depth and a majority of the plurality of recesses includes a second depth, and wherein the first depth is about equal to the second depth.

Embodiment 10

The absorbent article of embodiment 6, wherein a majority of the plurality of embossments includes a first depth, and wherein the first depth is greater than a greatest slit length in the intersecting slit formation.

Embodiment 11

The absorbent article of embodiment 6, wherein a majority of the plurality of embossments includes a first depth, wherein a majority of the plurality of recesses includes a second depth, the first depth is less than the second depth, a greatest slit length in the intersecting slit formation being less than or equal to a difference between the second depth and the first depth.

Embodiment 12

The absorbent article of embodiment 2, wherein the recess of the acquisition layer extends through the acquisition layer from the body facing surface of the acquisition layer to the garment facing surface of the acquisition layer.

Embodiment 13

The absorbent article of embodiment 2, wherein the body facing liner includes a plurality of embossments and the acquisition layer includes a plurality of recesses, at least some of the plurality of recesses receiving one of the plurality of embossments of the body facing liner in a nested configuration, a majority of the plurality of recesses of the acquisition layer extending through the acquisition layer from the body facing surface of the acquisition layer to the garment facing surface of the acquisition layer.

Embodiment 14

The absorbent article of embodiment 5, wherein a majority of the plurality of recesses of the acquisition layer do not extend through the acquisition layer from the body facing surface of the acquisition layer to the garment facing surface of the acquisition layer.

Embodiment 15

The absorbent article of any one of the preceding embodiments, wherein the acquisition layer includes a first layer and a second layer.

Embodiment 16

The absorbent article of embodiment 15, wherein the first layer includes fibers of a first average denier, and the second layer includes fibers of a second average denier, wherein the first average denier is greater than the second average denier.

Embodiment 17

The absorbent article of any one of the preceding embodiments, wherein the acquisition layer includes at least one channel.

Embodiment 18

The absorbent article of embodiment 5, wherein the acquisition layer includes at least one channel, the at least one channel extends from a first recess of the plurality of recesses to a second recess of the plurality of recesses.

Embodiment 19

The absorbent article of embodiment 5, wherein the acquisition layer includes a plurality of channels, wherein at least some of the plurality of channels extend from a first recess to a second recess of the plurality of recesses.

Embodiment 20

The absorbent article of embodiment 1 or embodiment 2, wherein the at least one embossment includes a first volume and the at least one recess defines a second volume, and wherein the first volume is at least about ten percent less than the second volume.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a longitudinal axis and a lateral axis, the absorbent article comprising:
    a front waist region, a rear waist region, a crotch region, the crotch region being disposed between the front waist region and the rear waist region;
    a front waist edge in the front waist region, a rear waist edge in the rear waist region, and a first longitudinal side edge and a second longitudinal side edge, the first longitudinal side edge and the second longitudinal side edge each extending from the front waist edge to the rear waist edge;
    a body facing liner including a body facing surface and a garment facing surface, the body facing liner including at least one embossment, the embossment including an intersecting slit formation;
    a backsheet;
    an absorbent body disposed between the body facing liner and the backsheet; and
    an acquisition layer including a body facing surface and a garment facing surface, the acquisition layer including at least one recess, the at least one recess receiving the at least one embossment of the body facing liner in a nested configuration;
    wherein the body facing liner includes a plurality of embossments and the acquisition layer includes a plurality of recesses, at least some of the plurality of recesses receiving one of the plurality of embossments of the body facing liner in a nested configuration;

wherein a majority of the plurality of embossments includes an intersecting slit formation, wherein a majority of the plurality of embossments includes a first depth, and wherein the first depth is greater than a greatest slit length in the intersecting slit formation.

2. An absorbent article including a longitudinal axis and a lateral axis, the absorbent article comprising:
- a front waist region, a rear waist region, a crotch region, the crotch region being disposed between the front waist region and the rear waist region;
- a front waist edge in the front waist region, a rear waist edge in the rear waist region, and a first longitudinal side edge and a second longitudinal side edge, the first longitudinal side edge and the second longitudinal side edge each extending from the front waist edge to the rear waist edge;
- a body facing liner including a body facing surface and a garment facing surface, the body facing liner including at least one embossment, the embossment including an intersecting slit formation;
- a backsheet;
- an absorbent body disposed between the body facing liner and the backsheet; and
- an acquisition layer including a body facing surface and a garment facing surface, the acquisition layer including at least one recess, the at least one recess receiving the at least one embossment of the body facing liner in a nested configuration;

wherein the body facing liner includes a plurality of embossments and the acquisition layer includes a plurality of recesses, at least some of the plurality of recesses receiving one of the plurality of embossments of the body facing liner in a nested configuration;

wherein a majority of the plurality of embossments includes an intersecting slit formation, wherein a majority of the plurality of embossments includes a first depth, wherein a majority of the plurality of recesses includes a second depth, the first depth is less than the second depth, a greatest slit length in the intersecting slit formation being less than or equal to a difference between the second depth and the first depth.

* * * * *